(12) United States Patent
Carle et al.

(10) Patent No.: US 11,179,305 B2
(45) Date of Patent: *Nov. 23, 2021

(54) TOPICAL COMPOSITIONS

(71) Applicant: MARY KAY INC., Addison, TX (US)

(72) Inventors: Tiffany Carle, Dallas, TX (US);
Michael Frushour, Addison, TX (US);
David Gan, Southlake, TX (US);
Geetha Kalahasti, Plano, TX (US);
Patricia Jacoby, Dallas, TX (US)

(73) Assignee: MARY KAY INC., Addison, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/898,120

(22) Filed: Jun. 10, 2020

(65) Prior Publication Data

US 2020/0297600 A1    Sep. 24, 2020

Related U.S. Application Data

(63) Continuation of application No. 15/233,451, filed on Aug. 10, 2016, now Pat. No. 10,722,436.

(60) Provisional application No. 62/203,155, filed on Aug. 10, 2015.

(51) Int. Cl.

| A61K 8/34 | (2006.01) |
|---|---|
| A61K 8/64 | (2006.01) |
| A61K 8/11 | (2006.01) |
| A61K 8/97 | (2017.01) |
| A61K 8/60 | (2006.01) |
| A61Q 17/04 | (2006.01) |
| A61Q 19/10 | (2006.01) |
| A61Q 19/08 | (2006.01) |
| A61Q 19/02 | (2006.01) |
| A61K 8/67 | (2006.01) |
| A61K 8/9711 | (2017.01) |
| A61K 8/9789 | (2017.01) |
| A61K 8/9706 | (2017.01) |

(52) U.S. Cl.
CPC ............ A61K 8/347 (2013.01); A61K 8/11 (2013.01); A61K 8/606 (2013.01); A61K 8/64 (2013.01); A61K 8/675 (2013.01); A61K 8/97 (2013.01); A61K 8/9706 (2017.08); A61K 8/9711 (2017.08); A61K 8/9789 (2017.08); A61Q 17/04 (2013.01); A61Q 19/02 (2013.01); A61Q 19/08 (2013.01); A61Q 19/10 (2013.01); A61K 2800/782 (2013.01)

(58) Field of Classification Search
None
See application file for complete search history.

(56) References Cited

U.S. PATENT DOCUMENTS

| 363,097 | A | 5/1887 | Traxler |
|---|---|---|---|
| 2,798,053 | A | 7/1957 | Brown |
| 3,755,560 | A | 8/1973 | Dickert et al. |
| 4,096,240 | A | 6/1978 | Mathur |
| 4,421,769 | A | 12/1983 | Dixon et al. |
| 4,509,949 | A | 4/1985 | Huang et al. |
| 4,599,379 | A | 7/1986 | Flesher et al. |
| 4,628,078 | A | 12/1986 | Glover et al. |
| 4,835,206 | A | 5/1989 | Farrar et al. |
| 4,849,484 | A | 7/1989 | Heard |
| 5,011,681 | A | 4/1991 | Ciotti et al. |
| 5,087,445 | A | 2/1992 | Haffey et al. |
| 5,100,660 | A | 3/1992 | Hawe et al. |
| 5,152,983 | A | 10/1992 | Nambudiry et al. |
| 5,254,331 | A | 10/1993 | Mausner |
| 5,508,033 | A | 4/1996 | Briand |
| 5,948,405 | A | 9/1999 | Cedro et al. |
| 6,605,296 | B1 | 8/2003 | Stuckler |
| 6,759,033 | B2 | 6/2004 | Zimmerman et al. |
| 6,989,150 | B1 | 1/2006 | Golz-Berner et al. |
| 7,014,842 | B2 | 3/2006 | Dueva-Koganov et al. |
| 7,090,872 | B2 | 8/2006 | Nagamine et al. |
| 7,722,904 | B2 | 5/2010 | Schneider et al. |
| 8,535,738 | B2 | 9/2013 | Collins et al. |
| 8,877,217 | B2 | 11/2014 | Kim et al. |
| 8,900,554 | B2 | 12/2014 | Tamarkin et al. |
| 9,192,560 | B2 | 11/2015 | Fournier |
| 9,233,061 | B2 | 1/2016 | Jang et al. |
| 9,241,965 | B2 | 1/2016 | Kim et al. |
| 2003/0144363 | A1 | 7/2003 | Liviero et al. |
| 2004/0081672 | A1 | 4/2004 | Gupta |
| 2004/0109905 | A1 | 6/2004 | Bagchi |

(Continued)

FOREIGN PATENT DOCUMENTS

| CN | 1200671 | 12/1998 |
|---|---|---|
| CN | 1203832 | 1/1999 |

(Continued)

OTHER PUBLICATIONS

Office Action issued in Corresponding Chinese Application No. 201680002651.1, dated Jul. 22, 2020 (English Translation provided).

Wang, Jianxin. *Encyclopedia of Cosmetic Plant Raw Material*, China Textile Press, 2012, p. 260, p. 396-397 (English Translation provided).

"Adenosine," Gottschalck, Tara E., and John E. Bailey eds., *International Cosmetic Ingredient Dictionary and Handbook*, 12th ed., vol. 1 Cosmetic, Toiletry, and Fragrance Association, 2008, 60.

(Continued)

Primary Examiner — Isis A Ghali
(74) Attorney, Agent, or Firm — Norton Rose Fulbright US LLP

(57) ABSTRACT

A method of reducing oxidative damage of skin is described. The method can include applying to oxidant damaged skin a topical composition that includes encapsulated resveratrol, oligopeptide-1, and niacinamide, wherein the combination of encapsulated resveratrol, oligopeptide-1, and niacinamide reduces oxidative damage in the skin, and wherein the oligopeptide-1 comprises the sequence of caprooyl-Gly-His-Lys-Lys.

16 Claims, No Drawings

(56) References Cited

U.S. PATENT DOCUMENTS

| | | |
|---|---|---|
| 2005/0163880 A1 | 7/2005 | Pusateri et al. |
| 2006/0074108 A1 | 4/2006 | Gupta |
| 2006/0280714 A1 | 12/2006 | Maningat et al. |
| 2008/0070368 A1 | 3/2008 | Kim et al. |
| 2009/0117211 A1 | 5/2009 | Schneider et al. |
| 2009/0297628 A1 | 12/2009 | Launay et al. |
| 2010/0004296 A1 | 1/2010 | Dannaker |
| 2010/0135935 A1 | 6/2010 | Leshchiner et al. |
| 2010/0150994 A1 | 6/2010 | Kotyla |
| 2010/0323045 A1 | 12/2010 | Pischel et al. |
| 2011/0206793 A1 | 8/2011 | Hines et al. |
| 2012/0171156 A1 | 7/2012 | Baskertter et al. |
| 2013/0156711 A1 | 6/2013 | Castro |
| 2013/0164391 A1 | 6/2013 | Kim et al. |
| 2013/0345309 A1 | 12/2013 | Shi et al. |
| 2014/0141035 A1 | 5/2014 | Sun et al. |
| 2014/0271507 A1 | 9/2014 | Morris-Irvin et al. |
| 2014/0275184 A1 | 9/2014 | Jones et al. |
| 2014/0308212 A1 | 10/2014 | Zhang |
| 2014/0323950 A1 | 10/2014 | Wirth |
| 2014/0356419 A1 | 12/2014 | Gujral et al. |
| 2015/0004255 A1 | 1/2015 | Rusai et al. |
| 2015/0005247 A1 | 1/2015 | Chen et al. |
| 2015/0038563 A1 | 2/2015 | Fournier |
| 2015/0202139 A1 | 7/2015 | Friedman |
| 2015/0328268 A1 | 11/2015 | Craciun et al. |
| 2015/0335560 A1 | 11/2015 | Bernard et al. |
| 2015/0342843 A1 | 12/2015 | Simmons |
| 2016/0008267 A1 | 1/2016 | Athwal |
| 2016/0120794 A1 | 5/2016 | Liu et al. |

FOREIGN PATENT DOCUMENTS

| | | |
|---|---|---|
| CN | 1125633 | 10/2003 |
| CN | 1133417 | 1/2004 |
| CN | 1145475 | 4/2004 |
| CN | 1146383 | 4/2004 |
| CN | 1198580 | 4/2005 |
| CN | 1787803 | 6/2006 |
| CN | 1882645 | 12/2006 |
| CN | 101014316 | 8/2007 |
| CN | 101190281 | 6/2008 |
| CN | 101267799 | 9/2008 |
| CN | 101291649 | 10/2008 |
| CN | 101360478 | 2/2009 |
| CN | 101579291 | 11/2009 |
| CN | 101669889 | 3/2010 |
| CN | 102065829 | 5/2011 |
| CN | 102123765 | 7/2011 |
| CN | 102614091 | 8/2012 |
| CN | 102871863 | 1/2013 |
| CN | 103037834 | 4/2013 |
| CN | 103494741 | 1/2014 |
| CN | 103501762 | 1/2014 |
| CN | 103550104 | 2/2014 |
| CN | 103767960 | 5/2014 |
| CN | 103826596 | 5/2014 |
| CN | 103826597 | 5/2014 |
| CN | 103826607 | 5/2014 |
| CN | 103841949 | 6/2014 |
| CN | 103857377 | 6/2014 |
| CN | 104173199 | 12/2014 |
| CN | 104302360 | 1/2015 |
| CN | 105050569 | 11/2015 |
| CN | 105658198 | 6/2016 |
| CN | 105708732 | 6/2016 |
| DE | 69007626 | 8/1994 |
| DE | 202012012801 | 2/2014 |
| EP | 490583 | 6/1992 |
| EP | 2510915 | 10/2012 |
| EP | 2522331 | 11/2012 |
| JP | H0867609 | 3/1996 |
| JP | 2502318 | 5/1996 |
| JP | 2013163643 | 8/2013 |
| KR | 1999-0040578 | 6/1999 |
| KR | 2001-0012902 | 2/2001 |
| KR | 2001-0022170 | 3/2001 |
| KR | 2003-0023398 | 3/2003 |
| KR | 2004-0101665 | 12/2004 |
| KR | 2006-0114090 | 11/2006 |
| KR | 2008-0053381 | 6/2008 |
| KR | 2008-0054627 | 6/2008 |
| KR | 2010-0102389 | 9/2010 |
| KR | 2011-0014221 | 2/2011 |
| KR | 2011-0028599 | 3/2011 |
| KR | 2011-0118705 | 10/2011 |
| KR | 2012-0058724 | 6/2012 |
| KR | 2012-0087716 | 8/2012 |
| KR | 2012-0001597 | 1/2013 |
| KR | 2013-0032420 | 4/2013 |
| KR | 2013-0048768 | 5/2013 |
| KR | 10-1321854 | 10/2013 |
| KR | 2013-0115309 | 10/2013 |
| KR | 2013-0115310 | 10/2013 |
| KR | 2014-0027947 | 3/2014 |
| KR | 2014-0069018 | 6/2014 |
| KR | 2014-0069019 | 6/2014 |
| KR | 2016-0093426 | 8/2016 |
| WO | WO 91/07946 | 6/1991 |
| WO | WO 96/14051 | 5/1996 |
| WO | WO 2007/083868 | 7/2007 |
| WO | WO 2009/003899 | 1/2009 |
| WO | WO 2009/138801 | 11/2009 |
| WO | WO 2011/162954 | 12/2011 |
| WO | WO 2012/154949 | 11/2012 |
| WO | WO 2013/149323 | 10/2013 |
| WO | WO 2013/190567 | 12/2013 |
| WO | WO 2014/059225 | 4/2014 |
| WO | WO 2014/078300 | 5/2014 |
| WO | WO 2014/079300 | 5/2014 |
| WO | WO 2014/086785 | 6/2014 |
| WO | WO 2014/197008 | 12/2014 |
| WO | WO 2015/004255 | 1/2015 |
| WO | WO 2015/085143 | 6/2015 |
| WO | WO 2015/100118 | 7/2015 |
| WO | WO 2015/161179 | 10/2015 |
| WO | WO 2015/172801 | 11/2015 |
| WO | WO 2016/000912 | 1/2016 |
| WO | WO 2016/036198 | 3/2016 |
| WO | WO 2016/069396 | 5/2016 |

OTHER PUBLICATIONS

"Niacinamide," Gottschalck, Tara E., and John E. Bailey eds., *International Cosmetic Ingredient Dictionary and Handbook*, 12$^{th}$ ed., vol. 2 Cosmetic, Toiletry, and Fragrance Association, 2008, 1651.

"Oligopeptide-1," Gottschalck, Tara E., and John E. Bailey eds., *International Cosmetic Ingredient Dictionary and Handbook*, 12$^{th}$ ed., vol. 2 Cosmetic, Toiletry, and Fragrance Association, 2008, 1722.

"*Opuntia ficus-indica* extract," Gottschalck, Tara E., and John E. Bailey eds., *International Cosmetic Ingredient Dictionary and Handbook*, 12$^{th}$ ed., vol. 2 Cosmetic, Toiletry, and Fragrance Association, 2008, 1730.

"*Opuntia tuna* fruit extract," Gottschalck, Tara E., and John E. Bailey eds., *International Cosmetic Ingredient Dictionary and Handbook*, 12$^{th}$ ed., vol. 2 Cosmetic, Toiletry, and Fragrance Association, 2008, 1731.

"Resveratrol," Gottschalck, Tara E., and John E. Bailey eds., *International Cosmetic Ingredient Dictionary and Handbook*, 12$^{th}$ ed., vol. 2 Cosmetic, Toiletry, and Fragrance Association, 2008, 2362.

Allemann et al., "Antioxidant used in skin care formulation", *Skin Therapy Letter* 2008, 13(7), 5-8.

Database GNPD [Online] MINTEL, "Hand & Décolleté Cream SPF 15", retrieved from URL < www.gnpd.com > database accession No. 1329412, May 25, 2010.

Database GNPD [Online] MINTEL, "Moisture Radiance Cream", retrieved from URL < www.gnpd.com > database accession No. 1375898, Aug. 1, 2010.

(56) References Cited

OTHER PUBLICATIONS

Database GNPD [Online] MINTEL, "Natural BB Cream", retrieved from URL < www.gnpd.com > database accession No. 1804103, Apr. 30, 2012.
Database GNPD [Online] MINTEL, "Serum", retrieved from URL < www.gnpd.com > database accession No. 1427618, Oct. 1, 2010.
Database GNPD [Online] MINTEL, "Thermal Fango Masque" retrieved from URL < www.gnpd.com > database accession No. 2285264, Jan. 10, 2014.
Database GNPD [Online] MINTEL, "Ultim-Age The Ultimate Anti-Ageing Serum", retrieved from URL < www.gnpd.com> database accession No. 1480536, Jan. 19, 2011.
Database GNPD [Online] MINTEL, "White Crystal BB Cream Spf 35/PA++", retrieved from URL www.gnpd.com >, database accession No. 1228953, Dec. 1, 2009.
Extended European Search Report issued in corresponding European U.S. Appl. No. 16/835,846, dated Feb. 20, 2019.
International Search Report and Written Opinion for PCT Application No. PCT/US/2016/046373 dated Nov. 21, 2016.
Malachite Extract, Gottschalck, Tara E., and John E. Bailey eds., *International Cosmetic Ingredient Dictionary and Handbook*, 12$^{th}$ ed., vol. 2 Cosmetic, Toiletry, and Fragrance Association, 2008, 1502.
Martin et al., "Resveratrol, a polyphenol found in grapes, suppresses oxidative damage and stimulates apoptosis during early colonic inflammation in rats", *Biochemical Pharmacology* 2004, 67, 1399-1410.
Patt et al. "Neova power defense combines biomimetic peptides with copper technology", *PhotoMedex* 2010, 4 pages.
Reddy et al., "Bioactive oligopeptides in dermatology: Part I", *Experimental Dermatology* 2012, 21, 563-568.
Sweet et al. "Effect of resveratrol on herps simplex virus vaginal infection in the mouse", *Antiviral Research* 2005, 67, 155-162.
Jin, Qingzhe. *Functional Lipids*. China Light Industry Press Ltd., 2013, pp. 167.
Jin, Yanzhen. *Skin Beauty*. Jilin Science and Technology Press Co., Ltd., 2010, pp. 171.
Office Action issued in Corresponding Chinese Application No. 201680002651.1, dated Mar. 30, 2021 (English Translation provided).
Search Report issued in Corresponding Chinese Application No. 201680002651.1, dated Mar. 22, 2021 (English Translation provided).
Yang et al., "Research Progress on Pharmacological Action of Nicotinamide" *Journal of Clinical Pulmonary Medicine* 2011, 16(12), 1914-1916.
Yoon et al., "Antioxidative Activity of the Extracts of Japanese Apricot (*Prunus mume* Sieb. et Zucc.)" *Korean J. Plant Res*. 2005, 8(3), 188-193.
Zhang, Guangjie. *Application Technology of Pharmaceutical Excipients*. China Medical Science Press, 1991, pp. 221.

TOPICAL COMPOSITIONS

CROSS-REFERENCE TO RELATED APPLICATIONS

This application is a continuation of U.S. application Ser. No. 15/233,451, filed Aug. 10, 2016, which claims the benefit of U.S. Provisional Application No. 62/203,155, filed Aug. 10, 2015. The contents of each of the referenced patent applications are incorporated into the present application by reference.

BACKGROUND OF THE INVENTION

A. Field of the Invention

The present invention relates generally to compositions that can be used to improve the skin's condition and/or visual appearance. In certain aspects, the compositions of the present invention can include, for example, a combination of ingredients to reduce fine lines and wrinkles, counter oxidative damage, reduce oxidizing agents, increase production of dermal proteins (such as collagen and elastin), reduce red blotches, reduce pigmentation in cells, inhibit tyrosinase, inhibit melanogenesis, and/or inhibit TNF-α. In other aspects, a combination of ingredients can reduce inflammation, increase moisture, reduce skin irritation, reduce dark circles in or under the eyes, inhibit MMP1, inhibit COX-1, inhibit COX-2, inhibit lipoxygenase, increase elastin production, increase collagen stimulation, increase laminin production, and/or reduce permeability of skin cells. This combination of ingredients can be included in a wide-range of product formulations (e.g., serums, eye creams, day creams, night creams, cleansers, toners, gels, masks, etc.).

B. Description of Related Art

Aging, chronic exposure to adverse environmental factors, malnutrition, fatigue, etc., can change the visual appearance, physical properties, or physiological functions of skin in ways that are considered visually undesirable. The most notable and obvious changes include the development of fine lines and wrinkles, loss of elasticity, increased sagging, loss of firmness, loss of color evenness or tone, coarse surface texture, and mottled pigmentation. Less obvious but measurable changes which occur as skin ages or endures chronic environmental insult include a general reduction in cellular and tissue vitality, reduction in cell replication rates, reduced cutaneous blood flow, reduced moisture content, accumulated errors in structure and function, alterations in the normal regulation of common biochemical pathways, and a reduction in the skin's ability to remodel and repair itself. Many of the alterations in appearance and function of the skin are caused by changes in the outer epidermal layer of the skin, while others are caused by changes in the lower dermis.

Many factors contribute to skin aging and the appearance of aging such as the actual age of a person, the amount of exposure to environmental factors (e.g., sun light, pollution, chemicals, smoke, etc.), and how well a person has taken care of their skin. In particular, skin aging concerns two processes—intrinsic aging, which is related to the natural aging process and genetic influences, and extrinsic aging, which is accumulated damage due to environmental factors.

Intrinsic aging process in cells and skin can be related to the loss of proper function of the skin in maintaining biochemical pathways. Such pathways can control the oxidative/reductive environment balance in the skin, the regulation of cell division and cellular membrane integrity, and the maintenance of the moisture balance of the skin. As one example, intrinsic aging can be due to the function of the protein Lamin A, which is important during cell division as it provides the membrane structure of the nuclease. Without functional Lamin A, the nuclear lamina creates an abnormal nuclear envelope lacking structural support. This can lead to an abnormal shaped nuclear envelope which limits cell division. A muted form of Lamin A, known as progerin, is associated with the disease progeria where patients suffer from accelerated aging, displaying signs of aging in skin as early as 2 years of age, and have a sharply shortened lifespan. This, and other losses of proper function of the skin can lead to loss of skin firmness, increased skin unevenness, increased fine lines and wrinkles, increased oxidative damage, and dry skin.

Extrinsic factors can include exposure to ultraviolet (UV) rays, irritants, and pollution. UV rays, through sun exposure or the use of ultraviolet lamps (for example, tanning beds), can induce oxidative stress, inflammation, production of melanin, and even genetic mutations that leads to skin damage. The accumulation of oxidative stress through free radical formation can damage skin proteins leading to skin aging, which includes loss of elasticity, loss of dermal proteins, lines and wrinkles, and abnormal pigmentation. Inflammation is also a characteristic of UV and environmental damage. Inflammation can occur through inflammatory cytokines such as TNF-α, or enzymes that contribute to the inflammatory pathway such as cyclooxygenase 1 (COX-1), cyclooxygenase 2 (COX-2), and lipoxygenase. As inflammation persists, enzymes such as matrix metalloproteinase-1 (MMP1), matrix metalloproteinase-3 (MMP3), and matrix metalloproteinase-9 (MMP9) are involved in the breakdown of dermal proteins, which allows immune cells to migrate. This breakdown in dermal proteins such as laminin, elastin, and collagen can lead to skin aging. When exposed to extrinsic factors, the keratinocyte (outermost cell of the skin) releases signaling molecules, such as α-melanocyte-stimulating hormone (α-MSH), and inflammatory cytokines. These hormones trigger melanocytes to produce melanin (melanogenesis). Tyrosine is converted to melanin in a two-step process that includes the use of the tyrosinase enzyme. The production of melanin can result in variations in the color of the skin. For example, a person's skin can have a sallow tone or hyperpigmented spots. Conventional depigmenting agents, such as hydroquinone, corticosteroids, and kojic acid can raise several safety concerns (for example, ochronosis, atrophy, carcinogenesis, and other local or systemic side effects) with long-term exposure.

Extrinsic factors can also reduce the moisture in skin. Exposure to chemicals, solvents, washing, cosmetics, fabrics, or dry environments are some of the many ways that skin can lose moisture. Loss of moisture can lead to breaks or fine lines and wrinkles in the skin.

The combination of intrinsic and extrinsic factors eventually leads to visible signs of aging. Current products on the market either do not effectively address the signs or causes of aging or the effects of extrinsic factors on the skin and/or they have skin irritating effects. For example, current products may not address loss of skin firmness, pigmentation problems, appearance of fine lines or wrinkles, and/or loss of moisture.

SUMMARY OF THE INVENTION

The inventors have determined a solution to the problems associated with current products to counteract some of the effects of aging and exposure to extrinsic factors that change the appearance and/or condition of skin. The solution resides in a combination of ingredients including any possible combination of encapsulated resveratrol, oligopeptide-1, niacinamide, *Opuntia ficus-indica* extract, *Prunus mume* extract, algae extract, malachite extract, adenosine, and/or *Opuntia tuna* fruit extract. The combination of ingredients can be used to create a topical skin composition to improve overall skin appearance, reduce fine lines, reduce wrinkles, improve radiance/luminosity, improve texture/smoothness, improve skin tone, improve firmness, improve elasticity, counter oxidative damage, reduce oxidizing agents, increase the oxidative capacity of a composition, increase production of dermal proteins (such as collagen and elastin), reduce red blotches, reduce pigmentation in cells, inhibit tyrosinase, inhibit melanogenesis, and/or inhibit TNF-α. The solution also provides compositions that reduce inflammation, increase moisture, reduce skin irritation, reduce dark circles in or under the eyes, inhibit MMP1, inhibit COX-1, inhibit COX-2, inhibit lipoxygenase, increase elastin production, increase collagen stimulation, increase laminin production, and/or reduce permeability of skin cells.

In one aspect, there is disclosed a topical composition. In one instance the topical composition includes any one of, any combination of, or all of encapsulated resveratrol, oligopeptide-1, and niacinamide. The amounts of the ingredients within the composition can vary (e.g., amounts can be as low as 0.000001% to as high as 98% w/w or any range therein). In one instance the composition further includes malachite extract. In some aspects, the malachite extract can be an extract of malachite stone and comprises a copper complex. In another instance, the composition further comprises water. In yet another instance, the composition includes 25% to 98% by weight of water. In one instance, the composition further includes *Opuntia tuna* fruit extract. In some aspects, the *Opuntia ficus-indica* extract can be a ferment of whole cactus plant. In another instance, the composition includes 0.00001% to 0.01% by weight of *Opuntia tuna* fruit extract. In yet another instance, the composition is formulated as an emulsion. In one instance the formulation is formulated as a cream. The composition may further comprise one or more ingredients described herein. For example, the composition may comprise one or more additional ingredients selected from one or more conditioning agents, moisturizing agents, pH adjusters, structuring agents, inorganic salts, and preservatives.

In another aspect, the topical composition above is formulated as a cleanser. In one instance, the topical composition above further comprises a skin exfoliating agent. A method of cleansing skin and/or hair is also disclosed. In one aspect, any one of the composition disclosed herein are used to cleanse skin and/or hair by applying any one of the compositions disclosed herein to skin and/or hair, and rinsing the composition off of the skin and/or hair. A method of exfoliating skin is also disclosed. In one aspect, any one of the composition disclosed herein are used to exfoliate skin by applying any one of the compositions disclosed herein to skin, wherein the skin is exfoliated.

In yet another aspect, the topical composition above further comprises *Opuntia ficus-indica* extract. In one instance, the topical composition further comprises a sunscreen ingredient. In another instance, the topical composition is formulated as a day cream. A method of protecting skin and/or hair from ultraviolet light is also disclosed. In one aspect, any one of the compositions disclosed herein are used to protect skin and/or hair from ultraviolet light by applying any one of the compositions disclosed herein to skin and/or hair, and leaving the composition on the skin and/or hair.

In one aspect, the topical composition above further comprises *Prunus mume* extract. In some instances, the *Prunus mume* extract is an aqueous extract. In some instances, the *Prunus mume* extract is an extract of *Prunus mume* leaf. In one instance, the topical composition is formulated as a night cream.

In another aspect, the topical composition above further comprises algae extract. In some aspects, the algae extract can be a water extract of *Fucus vesiculosus*. In one instance, the topical composition is formulated as an eye cream. A method of reducing a dark circle under or around the eye is also disclosed. In one aspect, the compositions disclosed herein are used to reduce a dark circle under or around the eye by applying any one of the compositions disclosed herein to skin around the eye, wherein the dark circle under or around the eye is reduced.

The compositions above may further comprise one or more ingredients described herein. For example, the composition may comprise one or more additional ingredients selected from one or more conditioning agents, moisturizing agents, pH adjusters, structuring agents, inorganic salts, and preservatives.

In one aspect, a topical composition is disclosed herein that contains encapsulated resveratrol, oligopeptide-1, and niacinamide, and optionally one or more of *Opuntia tuna* fruit extract, malachite extract, adenosine, *Prunus mume* leaf extract, algae extract, or *Opuntia ficus-indica* fruit extract. In some instances, oligopeptide-1 comprises the sequence of caprooyl-Gly-His-Lys-Lys, malachite extract is an extract of malachite stone and comprises a copper complex, the *Prunus mume* leaf extract is an aqueous extract, the algae extract is a water extract of *Fucus vesiculosus*, the *Opuntia ficus-indica* fruit extract is a ferment of whole cactus plant. The amounts of the ingredients within the composition can vary (e.g., amounts can be as low as 0.000001% to as high as 98% w/w or any range therein). In some instances, the composition contains 0.00001 to 0.1% by weight of encapsulated resveratrol, 0.0000001 to 0.01% by weight of oligopeptide-1, and 0.001 to 3% by weight of niacinamide. In some instances, the composition contains one or more of 0.00001 to 0.01% by weight of *Opuntia tuna* fruit extract, 0.00001 to 0.1% by weight of malachite extract, 0.001 to 1% by weight of adenosine, 0.01 to 3% by weight of *Prunus mume* leaf extract, 0.001 to 1% by weight of algae extract, or 0.001 to 3% by weight of *Opuntia ficus-indica* fruit extract. In some instances, the composition contains an effective amount of one or more of: encapsulated resveratrol to increase antioxidant capacity of the composition; oligopeptide-1 to inhibit tyrosinase, increase production of elastin, stimulate collagen production and/or secretion, and/or inhibit TNF-α; niacinamide to inhibit melanogenesis; *Opuntia tuna* fruit extract to inhibit COX-1, inhibit COX-2, inhibit lipoxygenase, and/or inhibit TNF-α; malachite extract to inhibit MMP1, inhibit COX-1, inhibit COX-2, inhibit lipoxygenase, and/or to increase antioxidant capacity of the composition; *Prunus mume* leaf extract to stimulate collagen production and/or secretion, increase laminin production, and/or increase antioxidant capacity of the composition; algae extract to increase skin barrier integrity; and/or *Opuntia ficus-indica* fruit extract to inhibit COX-1, inhibit COX-2, inhibit lipoxygenase, and/or inhibit TNF-α. In some instances, the composition further contains water. In some instances, the composition contains 25 to 98% by weight of water. In some instances, the composition contains glycerin and disodium EDTA. In some instances, the composition contains 0.0001 to 15% by weight of glycerin and 0.001 to 1% by weight of disodium EDTA. In some instances, the composition is formulated as an emulsion or a surfactant system.

In another aspect, the topical composition described above contains algae extract. In some instances, the composition contains 0.001 to 1% by weight of algae extract. In some instances, the composition contains glyceryl stearate and PEG-100 stearate. In some instances, the composition contains 0.1 to 5% by weight of glyceryl stearate and 0.01 to 3% by weight of PEG-100 stearate. In some instances, the composition further contains cetyl alcohol, C12-15 alkyl benzoate, stearic acid, and 1,2-hexanediol. In some instances, the composition further contains, 0.1 to 10% by weight of cetyl alcohol, 0.1 to 10% by weight of C12-15 alkyl benzoate, 0.1 to 5% by weight of stearic acid, and 0.01 to 3% by weight of 1,2-hexanediol. In some instances, the composition further contains, triethanolamine, benzyl alcohol, ethylhexyl palmitate, silica, mica, titanium dioxide, xanthan gum, dimethicone, and dipotassium glycyrrhizate. In some instances, the composition further contains, 0.01 to 3% by weight of triethanolamine, 0.01 to 3% by weight of benzyl alcohol, 0.01 to 3% by weight of ethylhexyl palmitate, 0.01 to 3% by weight of silica, 0.01 to 1% by weight of mica, 0.01 to 1% by weight of titanium dioxide, 0.01 to 1% by weight of xanthan gum, 0.01 to 1% by weight of dimethicone, and 0.001 to 1% by weight of dipotassium glycyrrhizate. In some instances, the composition is an emulsion. In some instances, the composition is formulated as an emulsion for an eye area. In some instances, the composition is formulated to decrease dark circles and/or puffiness in an eye area.

In one aspect, the topical composition described above contains *Opuntia ficus-indica* fruit extract and optionally one or more of malachite extract, *Opuntia tuna* fruit extract, and/or adenosine. In some instances, the composition contains 0.00001 to 0.01% by weight of *Opuntia ficus-indica* fruit extract and optionally one or more of 0.00001 to 0.1% by weight of malachite extract, 0.00001 to 3% by weight of *Opuntia tuna* fruit extract, and/or 0.001 to 1% adenosine. In some instances, the composition further contains at least one UV absorption and/or reflecting agent. In some instances, the at least one UV absorption and/or reflecting agent comprises homosalate, ethylhexyl salicylate (octisalate), oxybenzone, avobenzone, and octocrylene. In some instances, the composition contains 5 to 15% by weight of homosalate, 1 to 10% by weight of ethylhexyl salicylate (octisalate), 1 to 10% by weight of oxybenzone, 1 to 10% by weight of avobenzone, and 1 to 10% by weight of octocrylene. In some instances, the composition further contains ammonium acryloyldimethyltaurate/VP copolymer, ceteareth-25, and disodium ethylene dicocamide PEG-15 disulfate. In some instances, the composition contains 0.1 to 5% by weight of ammonium acryloyldimethyltaurate/VP copolymer, 0.01 to 3% by weight of ceteareth-25, and 0.01 to 3% by weight of disodium ethylene dicocamide PEG-15 disulfate. In some instances, the composition further contains dicaprylyl carbonate, cetearyl alcohol, and dimethicone. In some instances, the composition contains 0.1 to 5% by weight of dicaprylyl carbonate, 0.1 to 5% by weight of cetearyl alcohol, and 0.1 to 5% by weight of dimethicone. In some instances, the composition further contains phenoxyethanol, hydroxyacetophenone, silica, methyldihydrojasmonate, ethylene brassylate, bisabolol, caprylyl glycol, decylene glycol, and tocopheryl acetate. In some instances, the composition contains 0.01 to 3% by weight of phenoxyethanol, 0.01 to 3% by weight of hydroxyacetophenone, 0.01 to 1% by weight of silica, 0.01 to 1% by weight of methyldihydrojasmonate, 0.01 to 1% by weight of ethylene brassylate, 0.01 to 1% by weight of bisabolol, 0.01 to 1% by weight of caprylyl glycol, 0.001 to 1% by weight of decylene glycol, and 0.001 to 1% by weight of tocopheryl acetate. In some instances, the composition further contains jojoba esters and/or behenyl alcohol. In some instances, the composition contains 0.01 to 3% by weight of jojoba esters and/or 0.01 to 1% by weight of behenyl alcohol. In some instances, the composition is formulated as an emulsion. In some instances, the composition is formulated as a sunscreen emulsion.

In another aspect, the topical composition described above contains *Prunus mume* leaf extract and optionally one or more of malachite extract, *Opuntia tuna* fruit extract, and/or adenosine. In some instances, the composition contains 0.01 to 3% by weight of *Prunus mume* leaf extract and optionally one or more of 0.00001 to 0.1% by weight of malachite extract, 0.00001 to 3% by weight of *Opuntia tuna* fruit extract, and/or 0.001 to 1% adenosine. In some instances, the composition further contains glyceryl stearate and acrylamide/sodium acryloyldimethyltaurate copolymer. In some instances, the composition contains 0.01 to 3% by weight of glyceryl stearate and 0.01 to 3% by weight of acrylamide/sodium acryloyldimethyltaurate copolymer. In some instances, the composition further contains isohexadecane, dimethicone, aluminum starch octenylsuccinate, cetearyl alcohol, phenoxyethanol, butylene glycol, caprylic/capric triglyceride, methyldihydrojasmonate, and ethylene brassylate. In some instances, the composition contains 1 to 15% by weight of isohexadecane, 0.01 to 10% by weight of dimethicone, 1 to 10% by weight of aluminum starch octenylsuccinate, 0.1 to 5% by weight of cetearyl alcohol, 0.01 to 3% by weight of phenoxyethanol, 0.1 to 10% by weight of butylene glycol, 0.01 to 3% by weight of caprylic/capric triglyceride, 0.001 to 1% by weight of methyldihydrojasmonate, 0.001 to 1% by weight of ethylene brassylate. In some instances, the composition is formulated as an emulsion. In some instances, the composition is formulated as an emulsion gel. In some instances, the composition is formulated as a cream. In some instances, the composition is formulated as a night moisturizer. In some instances, the composition is formulated as a night moisturizer for the face.

In some instances, the topical composition described above that contains *Prunus mume* leaf extract and optionally one or more of malachite extract, *Opuntia tuna* fruit extract, and/or adenosine, further contains ceteareth-33 and ammonium acryloyldimethyltaurate/VP copolymer. In some instances, the composition contains 0.01 to 3% by weight of ceteareth-33 and 0.01 to 3% by weight of ammonium acryloyldimethyltaurate/VP copolymer. In some instances, the composition further contains pentylene glycol, isopropyl palmitate, panthenol, and dipotassium glycyrrhizate. In some instances, the composition contains 1 to 10% by weight of pentylene glycol, 0.01 to 3% by weight of isopropyl palmitate, 0.01 to 1% by weight of panthenol, and 0.001 to 1% by weight of dipotassium glycyrrhizate. In some instances, the composition is formulated as an emulsion. In some instances, the composition is formulated as an emulsion gel. In some instances, the composition is formulated as a cream. In some instances, the composition is formulated as a night moisturizer. In some instances, the composition is formulated as a night moisturizer for the face.

In some instances, the topical composition described above that contains *Prunus mume* leaf extract and optionally one or more of malachite extract, *Opuntia tuna* fruit extract, and/or adenosine, further contains isocetyl stearate, cetyl alcohol, cetyl esters, and caprylyl methicone. In some instances, the composition contains 0.1 to 5% by weight of isocetyl stearate, 0.1 to 5% by weight of cetyl alcohol, 0.1 to 5% by weight of cetyl esters, and 0.1 to 5% by weight of caprylyl methicone. In some instances, the composition further contains hydroxyacetophenone, stearic acid, PEG-100 stearate, arachidyl alcohol, triethanolamine, ceteareth-20, caprylyl glycol, behenyl alcohol, titanium dioxide, decylene glycol, tocopheryl acetate, polysorbate 80, and acrylates/C10-13 alkyl acrylate crosspolymer. In some instances, the composition contains 0.01 to 3% by weight of hydroxyacetophenone, 0.01 to 3% by weight of stearic acid, 0.01 to 3% by weight of PEG-100 stearate, 0.01 to 3% by weight of arachidyl alcohol, 0.01 to 3% by weight of triethanolamine, 0.01 to 1% by weight of ceteareth-20, 0.01 to 1% by weight of caprylyl glycol, 0.01 to 1% by weight of behenyl alcohol, 0.01 to 1% by weight of titanium dioxide, 0.001 to 1% by weight of decylene glycol, 0.001 to 1% by weight of tocopheryl acetate, 0.001 to 1% by weight of polysorbate 80, and 0.001 to 1% by weight of acrylates/C10-13 alkyl acrylate crosspolymer. In some instances, the composition is formulated as an emulsion. In some instances, the composition is formulated as an emulsion gel. In some instances, the composition is formulated as a cream. In some instances, the composition is formulated as a night moisturizer. In some instances, the composition is formulated as a night moisturizer for the face.

In one aspect, the topical composition described above optionally contains one or more of malachite extract and/or *Opuntia tuna* fruit extract. In some instances, the composition optionally contains one or more of 0.00001 to 0.1% by weight of malachite extract and/or 0.00001 to 3% by weight of *Opuntia tuna* fruit extract. In some instances, the composition further contains acrylates copolymer, magnesium aluminum silicate, sodium stearoyl glutamate, sodium cocoyl glutamate, cocamidopropyl betaine, PPG-2 hydroxyethyl coco/isostearamide, sodium laureth sulfate, and coco-glucoside. In some instances, the composition contains 1 to 10% by weight of acrylates copolymer, 0.01 to 3% by weight of magnesium aluminum silicate, 1 to 10% by weight of sodium stearoyl glutamate, 1 to 10% by weight of sodium cocoyl glutamate, 1 to 10% by weight of cocamidopropyl betaine, 1 to 10% by weight of PPG-2 hydroxyethyl coco/isostearamide, 0.01 to 3% by weight of sodium laureth sulfate, and 0.01 to 3% by weight of coco-glucoside. In some instances, the composition further contains cetearyl alcohol, propanediol, hydrolyzed corn starch, and potassium hydroxide. In some instances, the composition contains 1 to 10% by weight of cetearyl alcohol, 1 to 10% by weight of propanediol, 0.1 to 5% by weight of hydrolyzed corn starch, and 0.01 to 3% by weight of potassium hydroxide. In some instances, the composition further contains methyldihydrojasmonate, ethylene brassylate, sodium chloride, *Copernicia cerifera* (Carnauba) wax, citric acid, titanium dioxide, lactose, hydroxypropyl cyclodextrin, and tetramethyl acetyloctahydronaphthalenes. In some instances, the composition contains 0.01 to 1% by weight of methyldihydrojasmonate, 0.01 to 1% by weight of ethylene brassylate, 0.01 to 1% by weight of sodium chloride, 0.01 to 1% by weight of *Copernicia cerifera* (Carnauba) wax, 0.01 to 1% by weight of citric acid, 0.01 to 1% by weight of titanium dioxide, 0.001 to 1% by weight of lactose, 0.001 to 1% by weight of hydroxypropyl cyclodextrin, and 0.001 to 1% by weight of tetramethyl acetyloctahydronaphthalenes. In some instances, the composition is formulated as a surfactant system. In some instances, the composition is formulated as a cleanser. In some instances, the composition is formulated as a facial cleanser.

In another aspect, the topical composition disclosed above further contains acrylates copolymer, TEA-lauryl sulfate, cocamidopropyl betaine, and PPG-2 hydroxyethyl coco/isostearamide and optionally contains one or more of malachite extract and/or *Opuntia tuna* fruit extract and. In some instances, the composition optionally contains one or more of 0.00001 to 0.1% by weight of malachite extract and/or 0.00001 to 3% by weight of *Opuntia tuna* fruit extract. In some instances, the composition contains 1 to 10% by weight of acrylates copolymer, 5 to 20% by weight of TEA-lauryl sulfate, 0.1 to 5% by weight of cocamidopropyl betaine, and 0.1 to 5% by weight of PPG-2 hydroxyethyl coco/isostearamide. In some instances, the composition further contains propanediol and triethanolamine. In some instances, the composition contains 1 to 10% by weight of propanediol and 0.1 to 5% by weight of triethanolamine. In some instances, the composition further contains *Copernicia cerifera* (Carnauba) wax, sodium chloride, lactose, and hydroxypropyl cyclodextrin. In some instances, the composition contains 0.01 to 1% by weight of *Copernicia cerifera* (Carnauba) wax, 0.01 to 1% by weight of sodium chloride, 0.001 to 1% by weight of lactose, and 0.001 to 1% by weight of hydroxypropyl cyclodextrin. In some instances, the composition is formulated as a surfactant system. In some instances, the composition is formulated as a cleanser. In some instances, the composition is formulated as a facial cleanser.

Methods of using the compositions disclosed herein are also disclosed. In one aspect, a method is disclosed of improving a condition or appearance of skin and/or hair by applying any of the compositions disclosed herein to skin and/or hair in need thereof. In some instances, the condition or appearance of skin to be improved is the appearance of a fine line and/or wrinkle and the appearance of a fine line and/or wrinkle of the skin is reduced. In some instances, the condition or appearance of skin improved is a brightening of the skin and the brightness of the skin is increased. In some instances, the condition or appearance of skin improved is reduction of pigmentation of the skin and pigmentation of skin is reduced. In some instances, the condition or appearance of skin improved is reduction of a red blotch on skin and the red blotch on the skin is reduced. In some instances, the condition or appearance of skin improved is reduction of a dark circle under or around the eye, wherein the dark circle under or around the eye is reduced. In some instances, the condition or appearance of skin improved is the overall skin appearance and the overall skin appearance is improved. In some instances, the condition or appearance of skin improved is radiance/luminosity and the radiance/luminosity is improved. In some instances, the condition or appearance of skin improved is texture/smoothness and the texture/smoothness is improved. In some instances, the condition or appearance of skin improved is the skin tone and the skin tone is improved. In some instances, the condition or appearance of skin improved is firmness and the firmness is improved. In some instances, the condition or appearance of skin improved is elasticity and the elasticity is improved.

In another one aspect, a method is disclosed of treating skin and/or hair, by applying any of the compositions disclosed herein to skin and/or hair, wherein melanogenesis is reduced, tyrosinase is reduced, collagen stimulation is increased, elastin production is increased, inflammation is reduced, TNF-α is reduced, an oxidant is reduced, oxidative damage of the skin and/or hair by an oxidant is prevented, MMP1 is inhibited, COX-1 is inhibited, COX-2 is inhibited, lipoxygenase is inhibited, laminin production is increased, skin permeability is reduced, skin and/or hair is moisturized.

In one aspect, a method is disclosed of cleansing skin and/or hair, by applying any of the compositions disclosed herein to skin and/or hair, and rinsing the composition off of the skin and/or hair.

In another one aspect, a method is disclosed of protecting skin and/or hair from ultraviolet light, by applying any of the compositions disclosed herein to skin and/or hair, and leaving the composition on the skin and/or hair.

Methods of use for the compositions disclosed herein are also disclosed. In some aspects, a method is disclosed of improving a condition or appearance of skin and/or hair, by applying any one of the composition disclosed herein to skin and/or hair in need thereof. In one aspect, any one of the compositions disclosed herein are applied to skin and/or hair and the composition is left on the skin and/or hair, or alternatively removed from the skin and/or hair after a period of time. In another aspect, the compositions disclosed are used to reduce the appearance of a fine line and/or wrinkle, by applying any one of the composition disclosed herein to skin, wherein the appearance of a fine line and/or wrinkle of the skin is reduced. In yet another aspect, the compositions disclosed herein are used to moisturize skin and/or hair by applying any one of the compositions disclosed herein to skin and/or hair, wherein the skin and/or hair is moisturized.

Methods for using the compositions disclosed herein to brighten skin are also disclosed. In one aspect, the compositions disclosed herein are used to brighten skin by applying any one of the compositions disclosed herein to skin, wherein the brightness of the skin is increased. In another aspect, the compositions disclosed herein arc used to reduce pigmentation of skin by applying any one of the compositions disclosed herein to skin, wherein pigmentation of skin is reduced. In yet another aspect, the compositions disclosed herein are used to reduce a red blotch on skin by applying any one of the compositions disclosed herein to skin, wherein the red blotch on the skin is reduced. In one aspect, the compositions disclosed herein are used to reduce a dark circle under or around the eye by applying any one of the compositions disclosed herein to skin around the eye, wherein the dark circle under or around the eye is reduced. In another aspect, the compositions disclosed herein are used to inhibit melanogenesis in skin by applying any one of the compositions disclosed herein to skin, wherein melanogenesis in the skin is reduced. In yet another aspect, the compositions disclosed herein are used to inhibit tyrosinase in skin by applying any one of the compositions disclosed herein to skin, wherein tyrosinase in the skin is reduced.

Methods for using the compositions disclosed herein to increase production of proteins in the skin are also disclosed. In one aspect, the compositions disclosed herein are used to increase collagen stimulation in skin by applying any one of the compositions disclosed herein to skin, wherein collagen stimulation in skin is increased. In another aspect, the compositions disclosed herein are used to increase elastin production in skin by applying any one of the compositions disclosed herein to skin, wherein elastin production is increased. In yet another aspect, the compositions disclosed herein are used to increase laminin production in the skin by applying any one of the compositions disclosed herein to skin, wherein laminin production is increased.

Methods for using the compositions disclosed herein to provide additional benefits to the skin or hair are also disclosed. In one aspect, the compositions disclosed herein are used to reduce inflammation of skin by applying any one of the compositions disclosed herein to skin, wherein inflammation in the skin is reduced. In another aspect, the compositions disclosed herein are used to inhibit TNF-α in skin by applying any one of the compositions disclosed herein to skin, wherein TNF-α in the skin is reduced. In yet another aspect, the compositions disclosed herein are used to reduce an oxidant on and/or in the skin and/or hair by applying any one of the compositions disclosed herein to skin and/or hair, wherein the oxidant is reduced. In one aspect, the compositions disclosed herein are used to prevent oxidative damage to skin and/or hair by an oxidant by applying any one of the compositions disclosed herein to skin and/or hair, wherein an oxidant is reduced, and wherein oxidative damage to the skin and/or hair by the oxidant is prevented. In another aspect, the compositions disclosed herein are used to inhibit MMP1 in skin by applying any one of the compositions disclosed herein to skin, wherein MMP1 is inhibited in the skin. In another aspect, the compositions disclosed herein are used to inhibit COX-1 in skin by applying any one of the compositions disclosed herein to skin, wherein COX-1 is inhibited in the skin. In yet another aspect, the compositions disclosed herein are used to inhibit COX-2 in skin by applying any one of the compositions disclosed herein to skin, wherein COX-2 is inhibited in the skin. In one aspect, the compositions disclosed herein are used to inhibit lipoxygenase in skin by applying any one of the compositions disclosed herein to skin, wherein lipoxygenase is inhibited in the skin. In another aspect, the compositions disclosed herein are used to reduce skin permeability by applying any one of the compositions disclosed herein to skin, wherein skin permeability is reduced.

In particular aspects, the compositions of the present invention are formulated as a topical skin and/or hair composition. The composition can have a dermatologically acceptable vehicle or carrier for the compounds, compositions, and extracts. The composition can further include a moisturizing agent or a humectant, a surfactant, a silicone containing compounds, a UV agent, an oil, and/or other ingredients identified in this specification or those known in the art. The composition can be a lotion, cream, gel, serum, emulsion (e.g., oil-in-water, water-in-oil, silicone-in-water, water-in-silicone, water-in-oil-in-water, oil-in-water-in-oil, oil-in-water-in-silicone, etc.), solutions (e.g., aqueous or hydro-alcoholic solutions), anhydrous bases (e.g., lipstick or a powder), ointments, milk, paste, aerosol, solid forms, eye jellies, etc. The composition can be in powdered form (e.g., dried, lyophilized, particulate, etc.). The composition can be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, cps, etc., as measured on a Brookfield Viscometer using a TC spindle at 2.5 rpm at 25° C.).

The compositions of the present invention can also be modified to have a desired oxygen radical absorbance capacity (ORAC) value. In certain non-limiting aspects, the compositions of the present invention or the component or extracts thereof identified throughout this specification can be modified to have an ORAC value per mg of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 95, 100, 200, 300, 400, 500, 600, 700, 800, 900, 1000, 2000, 3000, 4000, 5000, 6000, 7000, 8000, 9000, 10000, 15000, 20000, 30000, 50000, 100000 or more or any range derivable therein.

The compositions in non-limiting aspects can have a pH of about 6 to about 9. In other aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride (e.g., caprylic capric triglyceride). The compositions can also include preservatives. Non-limiting examples of preservatives include methylparaben, propylparaben, or a mixture of methylparaben and propylparaben. In some aspects, the preservative is not a paraben.

Compositions of the present invention can have UVA and UVB absorption properties. The compositions can have an sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, or creams.

The compositions of the present invention can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, mist, dollop, or liquid. The container can include indicia on its surface. The indicia can be a word, an abbreviation, a picture, or a symbol.

It is also contemplated that the compositions disclosed throughout this specification can be used as a leave-on or rinse-off composition. By way of example, a leave-on composition can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or overnight or throughout the day). Alternatively, a rinse-off composition can be a product that is intended to be applied to the skin and then removed or rinsed from the skin (e.g., with water) within a period of time such as less than 5, 4, 3, 2, or 1 minute. An example of a rinse of composition can be a skin cleanser, shampoo, conditioner, or soap. An example of a leave-on composition can be a skin moisturizer, sunscreen, mask, overnight cream, or a day cream.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a gel, a wash, a cleanser, a foundation, a night cream, a day cream, and eye cream, a lipstick, a cleanser, a toner, a sunscreen, a mask, an anti-aging product, a deodorant, an antiperspirant, a perfume, a cologne, etc.

Also disclosed are the following Embodiments 1 to 97 of the present invention. Embodiment 1 is a method of improving a condition or appearance of skin and/or hair, comprising applying a topical composition comprising encapsulated resveratrol, oligopeptide-1, and niacinamide, and optionally one or more of *Opuntia tuna* fruit extract, malachite extract, adenosine, *Prunus mume* leaf extract, algae extract, or *Opuntia ficus-indica* fruit extract to skin and/or hair in need thereof. Embodiment 2 is the method of Embodiment 1, wherein the condition or appearance of skin to be improved is the appearance of a fine line and/or wrinkle, and further comprising wherein the appearance of a fine line and/or wrinkle of the skin is reduced. Embodiment 3 is the method of any of Embodiments 1 to 2, wherein the condition or appearance of skin to be improved is a brightening of the skin, and further comprising wherein the brightness of the skin is increased. Embodiment 4 is the method of any of Embodiments 1 to 3, wherein the condition or appearance of skin to be improved is reduction of pigmentation of the skin, and further comprising wherein pigmentation of skin is reduced. Embodiment 5 is the method of any of Embodiments 1 to 4, wherein the condition or appearance of skin to be improved is reduction of a red blotch on skin, and further comprising wherein the red blotch on the skin is reduced. Embodiment 6 is the method of any of Embodiments 1 to 5, wherein the condition or appearance of skin to be improved is reduction of a dark circle under or around the eye, and further comprising wherein the dark circle under or around the eye is reduced. Embodiment 7 is the method of any of Embodiments 1 to 6, wherein melanogenesis is reduced, tyrosinase is reduced, collagen stimulation is increased, elastin production is increased, inflammation is reduced, TNF-α is reduced, oxidative damage of the skin and/or hair is prevented, MMP1 is inhibited, COX-1 is inhibited, COX-2 is inhibited, lipoxygenase is inhibited, laminin production is increased, skin permeability is reduced, and/or skin and/or hair is moisturized. Embodiment 8 is the method of Embodiment 7, wherein the encapsulated resveratrol increases antioxidant capacity of the composition; oligopeptide-1 inhibits tyrosinase, increases production of elastin, stimulates collagen production and/or secretion, and/or inhibits TNF-α; niacinamide inhibits melanogenesis; *Opuntia tuna* fruit extract inhibits COX-1, inhibits COX-2, inhibits lipoxygenase, and/or inhibits TNF-α; malachite extract inhibits MMP1, inhibits COX-1, inhibits COX-2, inhibits lipoxygenase, and/or increases antioxidant capacity of the composition; *Prunus mume* leaf extract stimulates collagen production and/or secretion, increases laminin production, and/or increases antioxidant capacity of the composition; algae extract increases skin barrier integrity; and/or *Opuntia ficus-indica* fruit extract inhibits COX-1, inhibits COX-2, inhibits lipoxygenase, and/or inhibits TNF-α. Embodiment 9 is the method of any of Embodiments 1 to 8, wherein the oligopeptide-1 comprises the sequence of caprooyl-Gly-His-Lys-Lys, the malachite extract is an extract of malachite stone and comprises a copper complex, the *Prunus mume* leaf extract is an aqueous extract, the algae extract is a water extract of *Fucus vesiculosus*, the *Opuntia ficus-indica* fruit extract is a ferment of whole cactus plant. Embodiment 10 is the method of any of Embodiments 1 to 9, wherein the topical composition comprises 0.00001 to 0.1% by weight of encapsulated resveratrol, 0.0000001 to 0.01% by weight of oligopeptide-1, and 0.001 to 3% by weight of niacinamide. Embodiment 11 is the method of any of Embodiments 1 to 10, wherein the topical composition comprises one or more of 0.00001 to 0.01% by weight of *Opuntia tuna* fruit extract, 0.00001 to 0.1% by weight of malachite extract, 0.001 to 1% by weight of adenosine, 0.01 to 3% by weight of *Prunus mume* leaf extract, 0.001 to 1% by weight of algae extract, or 0.001 to 3% by weight of *Opuntia ficus-indica* fruit extract. Embodiment 12 is the method of any of Embodiments 1 to 11, wherein the skin and/or hair is cleansed, comprising applying the topical composition to skin and/or hair, and rinsing the composition off of the skin and/or hair. Embodiment 13 is the method of any of Embodiments 1 to 11, wherein the skin and/or hair is protected from ultraviolet light, comprising applying the topical composition to skin and/or hair, and leaving the composition on the skin and/or hair. Embodiment 14 is a topical composition comprising encapsulated resveratrol, oligopeptide-1, and niacinamide, and optionally one or more of *Opuntia tuna* fruit extract, malachite extract, adenosine, *Prunus mume* leaf extract, algae extract, or *Opuntia ficus-indica* fruit extract. Embodiment 15 is the composition of Embodiment 14, wherein the oligopeptide-1 comprises the sequence of caprooyl-Gly-His-Lys-Lys, the malachite extract is an extract of malachite stone and comprises a copper complex, the *Prunus mume* leaf extract is an aqueous extract, the algae extract is a water extract of *Fucus vesiculosus*, the *Opuntia ficus-indica* fruit extract is a ferment of whole cactus plant. Embodiment 16 is the composition of any of Embodiments 14 to 15, comprising 0.00001 to 0.1% by weight of encapsulated resveratrol, 0.0000001 to 0.01% by weight of oligopeptide-1, and 0.001 to 3% by weight of niacinamide. Embodiment 17 is the composition of any of Embodiments 14 to 16, comprising one or more of 0.00001 to 0.01% by weight of *Opuntia tuna* fruit extract, 0.00001 to 0.1% by weight of malachite extract, 0.001 to 1% by weight of adenosine, 0.01 to 3% by weight of *Prunus mume* leaf extract, 0.001 to 1% by weight of algae extract, or 0.001 to 3% by weight of *Opuntia ficus-indica* fruit extract. Embodiment 18 is the composition of any of Embodiments 14 to 17, wherein the composition comprises an effective amount of one or more of: encapsulated resveratrol to increase antioxidant capacity of the composition; oligopeptide-1 to inhibit tyrosinase, increase production of elastin, stimulate collagen production and/or secretion, and/or inhibit TNF-α; niacinamide to inhibit melanogenesis; *Opuntia tuna* fruit extract to inhibit COX-1, inhibit COX-2, inhibit lipoxygenase, and/or inhibit TNF-α; malachite extract to inhibit MMP1, inhibit COX-1, inhibit COX-2, inhibit lipoxygenase, and/or to increase antioxidant capacity of the composition; *Prunus mume* leaf extract to stimulate collagen production and/or secretion, increase laminin production, and/or increase antioxidant capacity of the composition; algae extract to increase skin barrier integrity; and/or *Opuntia ficus-indica* fruit extract to inhibit COX-1, inhibit COX-2, inhibit lipoxygenase, and/or inhibit TNF-α. Embodiment 19 is the composition of any of Embodiments 14 to 18, further comprising water. Embodiment 20 is the composition of any of Embodiments 14 to 19, comprising 25 to 98% by weight of water. Embodiment 21 is the composition of any of Embodiments 14 to 20, further comprising glycerin and disodium EDTA. Embodiment 22 is the composition of Embodiment 21, comprising 0.0001 to 15% by weight of glycerin and 0.001 to 1% by weight of disodium EDTA. Embodiment 23 is the composition of any of Embodiments 14 to 22, wherein the composition is formulated as an emulsion or a surfactant system. Embodiment 24 is the composition of any of Embodiments 14 to 23, wherein the composition comprises algae extract. Embodiment 25 is the composition of Embodiment 24, comprising 0.001 to 1% by weight of algae extract. Embodiment 26 is the composition of any of Embodiments 14 to 25, further comprising glyceryl stearate and PEG-100 stearate. Embodiment 27 is the composition of Embodiment 26, comprising 0.1 to 5% by weight of glyceryl stearate and 0.01 to 3% by weight of PEG-100 stearate. Embodiment 28 is the composition of any of Embodiments 14 to 27, further comprising cetyl alcohol, C12-15 alkyl benzoate, stearic acid, and 1,2-hexanediol. Embodiment 29 is the composition of Embodiment 28, comprising 0.1 to 10% by weight of cetyl alcohol, 0.1 to 10% by weight of C12-15 alkyl benzoate, 0.1 to 5% by weight of stearic acid, and 0.01 to 3% by weight of 1,2-hexanediol. Embodiment 30 is the composition of any of Embodiments 14 to 29, further comprising triethanolamine, benzyl alcohol, ethylhexyl palmitate, silica, mica, titanium dioxide, xanthan gum, dimethicone, and dipotassium glycyrrhizate. Embodiment 31 is the composition of Embodiment 30, comprising 0.01 to 3% by weight of triethanolamine, 0.01 to 3% by weight of benzyl alcohol, 0.01 to 3% by weight of ethylhexyl palmitate, 0.01 to 3% by weight of silica, 0.01 to 1% by weight of mica, 0.01 to 1% by weight of titanium dioxide, 0.01 to 1% by weight of xanthan gum, 0.01 to 1% by weight of dimethicone, and 0.001 to 1% by weight of dipotassium glycyrrhizate. Embodiment 32 is the composition of any of Embodiments 14 to 31, wherein the composition is an emulsion. Embodiment 33 is the composition of any of Embodiments 14 to 32, wherein the composition is formulated as an emulsion for an eye area. Embodiment 34 is the composition of any of Embodiments 14 to 33, wherein the composition is formulated to decrease dark circles and/or puffiness in an eye area. Embodiment 35 is the composition of any of Embodiments 14 to 23, wherein the composition comprises *Opuntia ficus-indica* fruit extract and optionally one or more of malachite extract, *Opuntia tuna* fruit extract, and/or adenosine. Embodiment 36 is the composition of Embodiment 35, comprising 0.00001 to 0.01% by weight of *Opuntia ficus-indica* fruit extract and optionally one or more of 0.00001 to 0.1% by weight of malachite extract, 0.00001 to 3% by weight of *Opuntia tuna* fruit extract, and/or 0.001 to 1% adenosine. Embodiment 37 is the composition of Embodiment 35 or 36, further comprising at least one UV absorption and/or reflecting agent. Embodiment 38 is the composition of Embodiment 37, wherein the at least one UV absorption and/or reflecting agent comprises homosalate, ethylhexyl salicylate (octisalate), oxybenzone, avobenzone, and octocrylene. Embodiment 39 is the composition of Embodiment 38, comprising 5 to 15% by weight of homosalate, 1 to 10% by weight of ethylhexyl salicylate (octisalate), 1 to 10% by weight of oxybenzone, 1 to 10% by weight of avobenzone, and 1 to 10% by weight of octocrylene. Embodiment 40 is the composition of any of Embodiments 35 to 39, further comprising ammonium acryloyldimethyltaurate/VP copolymer, ceteareth-25, and disodium ethylene dicocamide PEG-15 disulfate. Embodiment 41 is the composition of Embodiment 40, comprising 0.1 to 5% by weight of ammonium acryloyldimethyltaurate/VP copolymer, 0.01 to 3% by weight of ceteareth-25, and 0.01 to 3% by weight of disodium ethylene dicocamide PEG-15 disulfate. Embodiment 42 is the composition of any of Embodiments 35 to 41, further comprising dicaprylyl carbonate, cetearyl alcohol, and dimethicone. Embodiment 43 is the composition of Embodiment 42, comprising 0.1 to 5% by weight of dicaprylyl carbonate, 0.1 to 5% by weight of cetearyl alcohol, and 0.1 to 5% by weight of dimethicone. Embodiment 44 is the composition of any of Embodiments 35 to 43, further comprising phenoxyethanol, hydroxyacetophenone, silica, methyldihydrojasmonate, ethylene brassylate, bisabolol, caprylyl glycol, decylene glycol, and tocopheryl acetate. Embodiment 45 is the composition of Embodiment 44, comprising 0.01 to 3% by weight of phenoxyethanol, 0.01 to 3% by weight of hydroxyacetophenone, 0.01 to 1% by weight of silica, 0.01 to 1% by weight of methyldihydrojasmonate, 0.01 to 1% by weight of ethylene brassylate, 0.01 to 1% by weight of bisabolol, 0.01 to 1% by weight of caprylyl glycol, 0.001 to 1% by weight of decylene glycol, and 0.001 to 1% by weight of tocopheryl acetate. Embodiment 46 is the composition of any of Embodiments 35 to 45, further comprising jojoba esters and/or behenyl alcohol. Embodiment 47 is the composition of Embodiment 46, comprising 0.01 to 3% by weight of jojoba esters and/or 0.01 to 1% by weight of behenyl alcohol. Embodiment 48 is the composition of any of Embodiments 35 to 47, wherein the composition is formulated as an emulsion. Embodiment 49 is the composition of any of Embodiments 35 to 48, wherein the composition is formulated as a sunscreen emulsion. Embodiment 50 is the composition of any of Embodiments 14 to 23, wherein the composition comprises *Prunus mume* leaf extract and optionally one or more of malachite extract, *Opuntia tuna* fruit extract, and/or adenosine. Embodiment 51 is the composition of Embodiment 50, comprising 0.01 to 3% by weight of *Prunus mume* leaf extract and optionally one or more of 0.00001 to 0.1% by weight of malachite extract, 0.00001 to 3% by weight of *Opuntia tuna* fruit extract, and/or 0.001 to 1% adenosine. Embodiment 52 is the composition of Embodiment 50 or 51, further comprising glyceryl stearate and acrylamide/sodium acryloyldimethyltaurate copolymer Embodiment 53 is the composition of Embodiment 52, comprising 0.01 to 3% by weight of glyceryl stearate and 0.01 to 3% by weight of acrylamide/sodium acryloyldimethyltaurate copolymer. Embodiment 54 is the composition of any of Embodiments 50 to 53, further comprising isohexadecane, dimethicone, aluminum starch octenylsuccinate, cetearyl alcohol, phenoxyethanol, butylene glycol, caprylic/capric triglyceride, methyldihydrojasmonate, and ethylene brassylate. Embodiment 55 is the composition of Embodiment 54, comprising 1 to 15% by weight of isohexadecane, 0.01 to 10% by weight of dimethicone, 1 to 10% by weight of aluminum starch octenylsuccinate, 0.1 to 5% by weight of cetearyl alcohol, 0.01 to 3% by weight of phenoxyethanol, 0.1 to 10% by weight of butylene glycol, 0.01 to 3% by weight of caprylic/capric triglyceride, 0.001 to 1% by weight of methyldihydrojasmonate, 0.001 to 1% by weight of ethylene brassylate. Embodiment 56 is the composition of any of Embodiments 50 to 55, further comprising ceteareth-33 and ammonium acryloyldimethyltaurate/VP copolymer. Embodiment 57 is the composition of Embodiment 56, comprising 0.01 to 3% by weight of ceteareth-33 and 0.01 to 3% by weight of ammonium acryloyldimethyltaurate/VP copolymer. Embodiment 58 is the composition of any of Embodiments 50 to 57, further comprising pentylene glycol, isopropyl palmitate, panthenol, and dipotassium glycyrrhizate. Embodiment 59 is the composition of Embodiment 58, comprising 1 to 10% by weight of pentylene glycol, 0.01 to 3% by weight of isopropyl palmitate, 0.01 to 1% by weight of panthenol, and 0.001 to 1% by weight of dipotassium glycyrrhizate. Embodiment 60 is the composition of any of Embodiments 50 to 55, further comprising isocetyl stearate, cetyl alcohol, cetyl esters, and caprylyl methicone. Embodiment 61 is the composition of Embodiment 60, comprising 0.1 to 5% by weight of isocetyl stearate, 0.1 to 5% by weight of cetyl alcohol, 0.1 to 5% by weight of cetyl esters, and 0.1 to 5% by weight of caprylyl methicone. Embodiment 62 is the composition of any of Embodiments 60 to 61, further comprising hydroxyacetophenone, stearic acid, PEG-100 stearate, arachidyl alcohol, triethanolamine, ceteareth-20, caprylyl glycol, behenyl alcohol, titanium dioxide, decylene glycol, tocopheryl acetate, polysorbate 80, and acrylates/C10-13 alkyl acrylate crosspolymer. Embodiment 63 is the composition of Embodiment 62, comprising 0.01 to 3% by weight of hydroxyacetophenone, 0.01 to 3% by weight of stearic acid, 0.01 to 3% by weight of PEG-100 stearate, 0.01 to 3% by weight of arachidyl alcohol, 0.01 to 3% by weight of triethanolamine, 0.01 to 1% by weight of ceteareth-20, 0.01 to 1% by weight of caprylyl glycol, 0.01 to 1% by weight of behenyl alcohol, 0.01 to 1% by weight of titanium dioxide, 0.001 to 1% by weight of decylene glycol, 0.001 to 1% by weight of tocopheryl acetate, 0.001 to 1% by weight of polysorbate 80, and 0.001 to 1% by weight of acrylates/C10-13 alkyl acrylate crosspolymer. Embodiment 64 is the composition of any of Embodiments 50 to 57, wherein the composition is formulated as an emulsion. Embodiment 65 is the composition of any of Embodiments 50 to 64, wherein the composition is formulated as an emulsion gel. Embodiment 66 is the composition of any of Embodiments 50 to 65, wherein the composition is formulated as a cream. Embodiment 67 is the composition of any of Embodiments 50 to 66, wherein the composition is formulated as a night moisturizer. Embodiment 68 is the composition of any of Embodiments 50 to 67, wherein the composition is formulated as a night moisturizer for the face. Embodiment 69 is the composition of any of Embodiments 14 to 23, wherein the composition optionally comprises one or more of malachite extract and/or *Opuntia tuna* fruit extract. Embodiment 70 is the composition of Embodiment 69, optionally comprising one or more of 0.00001 to 0.1% by weight of malachite extract and/or 0.00001 to 3% by weight of *Opuntia tuna* fruit extract. Embodiment 71 is the composition of Embodiment 69 or 70, further comprising acrylates copolymer, magnesium aluminum silicate, sodium stearoyl glutamate, sodium cocoyl glutamate, cocamidopropyl betaine, PPG-2 hydroxyethyl coco/isostearamide, sodium laureth sulfate, and cocoglucoside. Embodiment 72 is the composition of Embodiment 71, comprising 1 to 10% by weight of acrylates copolymer, 0.01 to 3% by weight of magnesium aluminum silicate, 1 to 10% by weight of sodium stearoyl glutamate, 1 to 10% by weight of sodium cocoyl glutamate, 1 to 10% by weight of cocamidopropyl betaine, 1 to 10% by weight of PPG-2 hydroxyethyl coco/isostearamide, 0.01 to 3% by weight of sodium laureth sulfate, and 0.01 to 3% by weight of coco-glucoside. Embodiment 73 is the composition of any of Embodiments 69 to 72, further comprising cetearyl alcohol, propanediol, hydrolyzed corn starch, and potassium hydroxide. Embodiment 74 is the composition of Embodiment 73, comprising 1 to 10% by weight of cetearyl alcohol, 1 to 10% by weight of propanediol, 0.1 to 5% by weight of hydrolyzed corn starch, and 0.01 to 3% by weight of potassium hydroxide. Embodiment 75 is the composition of any of Embodiments 69 to 74, further comprising methyldihydrojasmonate, ethylene brassylate, sodium chloride, *Copernicia cerifera* (Carnauba) wax, citric acid, titanium dioxide, lactose, hydroxypropyl cyclodextrin, and tetramethyl acetyloctahydronaphthalenes. Embodiment 76 is the composition of Embodiment 75, comprising 0.01 to 1% by weight of methyldihydrojasmonate, 0.01 to 1% by weight of ethylene brassylate, 0.01 to 1% by weight of sodium chloride, 0.01 to 1% by weight of *Copernicia cerifera* (Carnauba) wax, 0.01 to 1% by weight of citric acid, 0.01 to 1% by weight of titanium dioxide, 0.001 to 1% by weight of lactose, 0.001 to 1% by weight of hydroxypropyl cyclodextrin, and 0.001 to 1% by weight of tetramethyl acetyloctahydronaphthalenes. Embodiment 77 is the composition of any of Embodiments 69 to 76, wherein the composition is formulated as a surfactant system. Embodiment 78 is the composition of any of Embodiments 69 to 77, wherein the composition is formulated as a cleanser. Embodiment 79 is the composition of any of Embodiments 69 to 78, wherein the composition is formulated as a facial cleanser. Embodiment 80 is the composition of any of Embodiments 69 to 70, further comprising acrylates copolymer, TEA-lauryl sulfate, cocamidopropyl betaine, and PPG-2 hydroxyethyl coco/isostearamide. Embodiment 81 is the composition of Embodiment 80, comprising 1 to 10% by weight of acrylates copolymer, 5 to 20% by weight of TEA-lauryl sulfate, 0.1 to 5% by weight of cocamidopropyl betaine, and 0.1 to 5% by weight of PPG-2 hydroxyethyl coco/isostearamide. Embodiment 82 is the composition of Embodiment 80 or 81, further comprising propanediol and triethanolamine. Embodiment 83 is the composition of Embodiment 82, comprising 1 to 10% by weight of propanediol and 0.1 to 5% by weight of triethanolamine. Embodiment 84 is the composition of any of Embodiments 80 to 83, further comprising *Copernicia cerifera* (Carnauba) wax, sodium chloride, lactose, and hydroxypropyl cyclodextrin. Embodiment 85 is the composition of Embodiment 84, comprising 0.01 to 1% by weight of *Copernicia cerifera* (Carnauba) wax, 0.01 to 1% by weight of sodium chloride, 0.001 to 1% by weight of lactose, and 0.001 to 1% by weight of hydroxypropyl cyclodextrin. Embodiment 86 is the composition of any of Embodiments 80 to 85, wherein the composition is formulated as a surfactant system. Embodiment 87 is the composition of any of Embodiments 80 to 86, wherein the composition is formulated as a cleanser. Embodiment 88 is the composition of any of Embodiments 80 to 87, wherein the composition is formulated as a facial cleanser. Embodiment 89 is the method of Embodiment 1, wherein the condition or appearance of skin to be improved is the overall skin appearance and the overall skin appearance is improved. Embodiment 90 is the method of Embodiment 1, wherein the condition or appearance of skin to be improved is radiance/luminosity and the radiance/luminosity is improved. Embodiment 91 is the method of Embodiment 1, wherein the condition or appearance of skin to be improved is skin texture/smoothness and the texture/smoothness is improved. Embodiment 92 is the method of Embodiment 1, wherein the condition or appearance of skin to be improved is the skin tone and the skin tone is improved. Embodiment 93 is the method of Embodiment 1, wherein the condition or appearance of skin to be improved is skin firmness and the firmness is improved. Embodiment 94 is the method of Embodiment 1, wherein the condition or appearance of skin to be improved is skin elasticity and the elasticity is improved. Embodiment 95 is the method of any of Embodiments 89 to 94, wherein the method comprises applying the topical composition daily to skin in need thereof. Embodiment 96 is the method of Embodiment 95, wherein the topical composition is applied twice daily. Embodiment 97 is the method of Embodiment 95, wherein the topical composition is applied as a cleanser twice daily, is applied as a day cream once daily, is applied as a night cream once daily, and/or is applied as an eye cream twice daily.

"Topical application" means to apply or spread a composition onto the surface of lips or keratinous tissue. "Topical skin composition" includes compositions suitable for topical application on lips or keratinous tissue. Such compositions are typically dermatologically-acceptable in that they do not have undue toxicity, incompatibility, instability, allergic response, and the like, when applied to lips or skin. Topical skin care compositions of the present invention can have a selected viscosity to avoid significant dripping or pooling after application to skin.

"Keratinous tissue" includes keratin-containing layers disposed as the outermost protective covering of mammals and includes, but is not limited to, lips, skin, hair and nails.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase or production of a protein or molecule (e.g., matrix proteins such as fibronectin, laminin, collagen, or clastin or molecules such as hyaluronic acid) to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

As noted above, several of the unique aspects of the present invention are to combine in a topical cosmetic composition encapsulated resveratrol, oligopeptide-1, niacinamide, *Opuntia ficus-indica* extract, *Prunus mume* extract, algae extract, malachite extract, adenosine, and/or *Opuntia tuna* fruit extract. This allows for the benefits reduce fine lines and wrinkles, counter oxidative damage, reduce oxidizing agents, increase production of dermal proteins (such as collagen and elastin), reduce red blotches, reduce pigmentation in cells, inhibit tyrosinase, inhibit melanogenesis, inhibit TNF-α, reduce inflammation, increase moisture, reduce skin irritation, reduce dark circles in or under the eyes, inhibit MMP1, inhibit COX-1, inhibit COX-2, inhibit lipoxygenase, increase elastin production, increase collagen stimulation, increase laminin production, and/or reduce permeability of skin cells.

The following subsections describe non-limiting aspects of the present invention in further detail.

A particular embodiment of the present invention is designed to work as an eye cream composition. In one instance, the eye cream can help firm up skin and increase microcirculation to reduce the appearance of under eye bags, reduce the appearance of dark circles, and/or prevent and/or address the signs of aging. The composition relies on a unique combination of any one of, any combination of, or all of encapsulated resveratrol, oligopeptide-1, niacinamide, *Opuntia ficus-indica* extract, *Prunus mume* extract, algae extract, malachite extract, adenosine, and/or *Opuntia tuna* fruit extract. In some embodiments, the composition contains a combination of encapsulated resveratrol, oligopeptide-1, niacinamide, and algae extract. In some embodiments, the composition additionally contains malachite extract. Examples of such a composition are provided in Example 1, Table 1 and Example 4, Table 14.

Another particular embodiment of the present invention is designed to work as a day cream. In one instance, the day cream can moisturize and protect from Ultraviolet light and/or prevent and/or address the signs of aging. The composition relies on a unique combination of any one of, any combination of, or all of encapsulated resveratrol, oligopeptide-1, niacinamide, *Opuntia ficus-indica* extract, *Prunus mume* extract, algae extract, malachite extract, adenosine, and/or *Opuntia tuna* fruit extract. In some embodiments, the composition contains a combination of encapsulated resveratrol, oligopeptide-1, niacinamide, and *Opuntia ficus-indica* extract. In some embodiments, the composition additionally contains adenosine. In some embodiments, the composition additionally contains malachite extract. In some embodiments, the composition additionally contains *Opuntia tuna* fruit extract. Examples of such compositions are provided in Example 1, Table 2 and Example 4, Table 15.

Another particular embodiment of the present invention is designed to work as a night cream. In one instance, the night cream can moisturize and/or prevent and/or address the signs of aging. The composition relies on a unique combination of any one of, any combination of, or all of encapsulated resveratrol, oligopeptide-1, niacinamide, *Opuntia ficus-indica* extract, *Prunus mume* extract, algae extract, malachite extract, adenosine, and/or *Opuntia tuna* fruit extract. In some embodiments, the composition contains a combination of encapsulated resveratrol, oligopeptide-1, niacinamide, and *Prunus mume* extract. In some embodiments, the composition additionally contains adenosine. In some embodiments, the composition additionally contains malachite extract. In some embodiments, the composition additionally contains *Opuntia tuna* fruit extract. Examples of such compositions are provided in Example 1, Table 3 and Example 4, Table 16 and 17.

Another particular embodiment of the present invention is designed to work as a cleanser. In one instance, the cleanser can exfoliate the skin, cleanse the skin and/or hair of excess oils, sebum, and/or particulates, and/or prevent or address the signs of aging. The composition relies on a unique combination of any one of, any combination of, or all of encapsulated resveratrol, oligopeptide-1, niacinamide, *Opuntia ficus-indica* extract, *Prunus mume* extract, algae extract, malachite extract, adenosine, and/or *Opuntia tuna* fruit extract. In some embodiments, the composition contains a combination of encapsulated resveratrol, oligopeptide-1, and niacinamide. In some embodiments, the composition additionally contains malachite extract. In some embodiments, the composition additionally contains *Opuntia tuna* fruit extract. Example of such compositions are provided in Example 1, Table 4 and Example 4, Tables 18 and 19.

Another particular embodiment of the present invention is designed to work as a foundation. In one instance, the foundation reduces the appearance of the signs of aging, acst as a base for the application of additional cosmetics, and/or prevents or addresses the signs of aging. The composition relies on a unique combination of any one of, any combination of, or all of encapsulated resveratrol, oligopeptide-1, niacinamide, *Opuntia ficus-indica* extract, *Prunus mume* extract, algae extract, malachite extract, adenosine, and/or *Opuntia tuna* fruit extract. In some embodiments, the composition contains a combination of encapsulated resveratrol, oligopeptide-1, and niacinamide. In some embodiments, the composition additionally contains malachite extract. In some embodiments, the composition additionally contains *Opuntia tuna* fruit extract. Example of such compositions are provided in Example 1, Table 5.

The above compositions can be applied to the skin or hair and remain on the skin or hair for a period of time (e.g., at least 1, 2, 3, 4, 5, 10, 20, 30, or 60 minutes or more). After which the composition, if needed, can be rinsed from the skin or peeled from the skin. The above compositions can also be applied to the skin and then rinsed or peeled from the skin.

A. Active Ingredients

The present invention is premised on a determination that a combination of active ingredients—encapsulated resveratrol, oligopeptide-1, and niacinamide—can be used to improve the skin's visual appearance and counteract the extrinsic and intrinsic effects of aging. As non-limiting examples, the three ingredients above when combined can reduce fine lines and wrinkles, counter oxidative damage, reduce oxidizing agents, increase the antioxidant capacity of a composition, increase production of dermal proteins (such as collagen and elastin), reduce red blotches, reduce pigmentation in cells, inhibit tyrosinase, inhibit melanogenesis, and/or inhibit TNF-α.

Additional active ingredients can also be used in combination with the above mentioned active ingredients. In one aspect, the active ingredients include one or more of *Opuntia ficus-indica* extract, *Prunus mume* extract, algae extract, malachite extract, adenosine, and/or *Opuntia tuna* fruit extract. The additional active ingredients can be used to improve the skin's visual appearance and/or counteract the extrinsic and intrinsic effects of aging. As non-limiting examples, these ingredients can reduce inflammation, increase moisture, reduce skin irritation, reduce dark circles in or under the eyes, inhibit MMP1, inhibit COX-1, inhibit COX-2, inhibit lipoxygenase, increase elastin production, increase collagen stimulation, increase laminin production, inhibit TNF-α, reduce an oxidant, and reduce permeability of skin cells.

The combination of ingredients can be used in different products to treat various skin conditions. By way of non-limiting examples, an eye cream can help firm up skin, increase microcirculation to reduce the appearance of under eye bags, reduce the appearance of dark circles, and/or prevent and/or address the signs of aging, a day cream can help moisturize and protect from Ultraviolet light and/or prevent and/or address the signs of aging, a night cream can moisturize and/or prevent and/or address the signs of aging, a cleanser can exfoliate skin, cleanse the skin and/or hair of excess oils, sebum, and/or particulates, and/or prevent or address the signs of aging. A regimen of the eye cream, day cream, night cream, and cleanser improves overall skin appearance, decreases facial and neck fine lines (sub-orbital and global), decreases wrinkles (sub-orbital and global), improves radiance/luminosity, improves texture/smoothness (visual and tactile), improves skin tone (clarity and evenness), improves firmness (visual), and improves elasticity (tactile).

Encapsulated resveratrol is an encapsulation of a natural phenol in concentric macrovesicles of surfactant and aqueous phase bilayers. Encapsulated resveratrol is commercially available and can be obtained from Silicones Plus under the trade name Spherulite-Res or Lipobeads Purple & Resveratrol DS60820 supplied by Vantage Specialty Chemicals. Non-limiting examples of the benefits provided by resveratrol and shown herein include anti-oxidant capacity.

Oligopeptide-1, also known as caprooyl-tetrapeptide-3, is a modified tetrapeptide having a sequence of caprooyl-Gly-His-Lys-Lys. Oligopeptide-1 is commercially available and can be obtained from Lucas Meyer under the trade name ChroNOline™. Non-limiting examples of the benefits provided by oligopeptide-1 and shown herein include inhibition of tyrosinase, increased production of elastin, increased stimulation of collagen, and/or inhibition of TNF-α.

Niacinamide, also known as nicotinamide, 3-Pyridinecarboxamide, or vitamin B3, is an organic compound known to exhibit skin conditioning benefits when used in cosmetic compositions. The compound is widely commercially available. Non-limiting examples of the benefits provided by niacinamide and shown herein include inhibition of melanogenesis.

*Opuntia ficus-indica* extract is a fermentation of whole cactus plant. The extract is commercially available and can be obtained from Barnet under the trade name Nopalex. Non-limiting examples of the benefits provided by *Opuntia ficus-indica* extract and shown herein include inhibition of COX-1, inhibition of COX-2, inhibition of lipoxygenase, and/or inhibition of TNF-α.

*Prunus mume* extract is an aqueous extract of *Prunus mume* leaf. *Prunus mume* is also known as Japanese Apricot. Non-limiting examples of the extraction method of *Prunus mume* extract includes extracting the leaves of *Prunus mume* using an aqueous solution and then placing the aqueous extract in butylene glycol. The extract is commercially available and can be obtained from Southern Cross/Lucas Meyer. Non-limiting examples of the benefits provided by *Prunus mume* extract and shown herein include anti-oxidant capacity, increased collagen stimulation, and increased laminin production.

Algae extract is a water extract of *Fucus vesiculosus*, a brown algae commonly known as bladderwrack. The extract is commercially available and can be obtained from BASF under the trade name Shadownyl™. Non-limiting examples of the benefits provided by algae extract and shown herein include reduced permeability of skin cells.

Malachite extract is an extract of malachite stone. The extract is a source of an anti-oxidant copper complex. The extract is commercially available and can be obtained from Gattefossé under the trade name Mala'Kîte™. Non-limiting examples of the benefits provided by malachite extract and shown herein include inhibition of MMP1, inhibition of COX-1, inhibition of COX-2, inhibition of lipoxygenase, and possession of antioxidant properties.

Adenosine is a purine nucleoside comprising a molecule of adenine attached to a ribose sugar molecule moiety. The compound is commercially available and can be obtained from a variety of commercial sources.

*Opuntia tuna* fruit extract is an extract from the fruit of prickly pear. The extract is commercially available and can be obtained from a variety of commercial sources (see International Cosmetic Ingredient Dictionary and Handbook, 12th edition, volume 2, page 1731 (2008), which is incorporated by reference).

The extracts described herein can be extracts made through extraction methods known in the art and combinations thereof. Non-limiting examples of extraction methods include the use of liquid-liquid extraction, solid phase extraction, aqueous extraction, ethyl acetate, alcohol, acetone, oil, supercritical carbon dioxide, heat, pressure, pressure drop extraction, ultrasonic extraction, etc. Extracts can be a liquid, solid, dried liquid, re-suspended solid, etc.

B. Amounts of Ingredients

It is contemplated that the compositions of the present invention can include any amount of the ingredients discussed in this specification. The compositions can also include any number of combinations of additional ingredients described throughout this specification (e.g., pigments, or additional cosmetic or pharmaceutical ingredients). The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

C. Vehicles

The compositions of the present invention can include or be incorporated into all types of vehicles and carriers. The vehicle or carrier can be a pharmaceutically or dermatologically acceptable vehicle or carrier. Non-limiting examples of vehicles or carriers include water, glycerin, alcohol, oil, a silicon containing compound, a silicone compound, and wax. Variations and other appropriate vehicles will be apparent to the skilled artisan and are appropriate for use in the present invention. In certain aspects, the concentrations and combinations of the compounds, ingredients, and agents can be selected in such a way that the combinations are chemically compatible and do not form complexes which precipitate from the finished product.

D. Structure

The compositions of the present invention can be structured or formulated into a variety of different forms. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, masks, peels, and ointments. Variations and other structures will be apparent to the skilled artisan and are appropriate for use in the present invention.

E. Additional Ingredients

In addition to the combination of ingredients disclosed by the inventors, the compositions can also include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrance agents (artificial and natural; e.g., gluconic acid, phenoxyethanol, and triethanolamine), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), flavoring agents/aroma agents (e.g., *Stevia rebaudiana* (sweetleaf) extract, and menthol), adsorbents, lubricants, solvents, moisturizers (including, e.g., emollients, humectants, film formers, occlusive agents, and agents that affect the natural moisturization mechanisms of the skin), water-repellants, UV absorbers and/or reflectors (physical and chemical absorbers such as para-aminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., Aloe vera, chamomile, cucumber extract, *Ginkgo biloba, ginseng*, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, methyl gluceth-20, saccharide isomerate, and mannitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, biosaccharide gum-1, ethylhexylglycerin, pentylene glycol, hydrogenated polydecene, octyldodecyl oleate, and dipotassium glycyrrhizate). Non-limiting examples of some of these ingredients are provided in the following subsections.

a. UV Absorption and/or Reflecting Agents

UV absorption and/or reflecting agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, saccharide isomerate, salts of pyrrolidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, Aloe barbadensis, Aloe barbadensis extract, Aloe barbadensis gel, Althea officinalis extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamom (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, *Geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, *Macadamia ternifolia* nut oil, maltitol, matricaria (*Chamomilla recutita*) oil, methyl glucose sesquistearate, methylsilanol PCA, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*Mentha piperita*) oil, petrolatum, phospholipids, plankton extract, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfate, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

g. Exfoliating Agent

Exfoliating agents include ingredients that remove dead skin cells on the skin's outer surface. These agents may act through mechanical, chemical, and/or other means. Non-limiting examples of mechanical exfoliating agents include abrasives such as pumice, silica, cloth, paper, shells, beads, solid crystals, solid polymers, etc. Non-limiting examples of chemical exfoliating agents include acids and enzyme exfoliants. Acids that can be used as exfoliating agents include, but are not limited to, glycolic acid, lactic acid, citric acid, alpha hydroxy acids, beta hydroxy acids, etc. Other exfoliating agents known to those of skill in the art are also contemplated as being useful within the context of the present invention.

h. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

i. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyltaurate/vp copolymer, or a mixture of them.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835, 206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

j. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

F. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Combinations of active ingredients disclosed herein can be included in a wide-range of topical product formulations for skin and/or hair. Combinations from Example 1 may be prepared as topical skin or hair compositions. In some aspects, the combination in Table 1 may be prepared as an eye cream. In some aspects, the combination in Table 2 may be prepared as day cream. In some aspects, the combination in Table 3 may be prepared as a night cream. In some aspects, the combination of Table 4 may be prepared as a cleanser. In some aspects, the combination of Table 5 may be prepared as a foundation.

All of the compositions disclosed and claimed herein can be made and executed without undue experimentation in light of the present disclosure. While the compositions and methods of this invention have been described in terms of preferred embodiments, it will be apparent to those of skill in the art that variations may be applied to the compositions and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

TABLE 1

| Eye Cream Ingredient |
|---|
| Encapsulated Resveratrol |
| Oligopeptide-1 |
| Niacinamide |
| Algae Extract |
| Malachite Extract (optional) |

TABLE 2

| Day Cream Ingredient |
|---|
| Encapsulated Resveratrol |
| Oligopeptide-1 |
| Niacinamide |

TABLE 2-continued

| Day Cream Ingredient |
|---|
| *Opuntia ficus-indica* extract |
| Malachite Extract (optional) |

TABLE 3

| Night Cream Ingredient |
|---|
| Encapsulated Resveratrol |
| Oligopeptide-1 |
| Niacinamide |
| *Prunus mume* extract |
| Malachite Extract (optional) |
| Adenosine (optional) |

TABLE 4

| Cleanser Ingredient |
|---|
| Encapsulated Resveratrol |
| Oligopeptide-1 |
| Niacinamide |
| Malachite Extract (optional) |

TABLE 5

| Foundation Ingredient |
|---|
| Encapsulated Resveratrol |
| Oligopeptide-1 |
| Niacinamide |
| Malachite Extract (optional) |

Example 2

Tables 6 and 7 describe generic formulations or skin testing formulations in which an active ingredient can be incorporated into. These formulations can also be used to determine the types of skin benefits that can be attributed to the active ingredient. These formulations are prepared in such a manner that any resulting skin benefit from topical application of the formula to skin can be directly attributed to the active ingredient being tested. In the context of aspects of the present invention, the active ingredient that can be tested can be encapsulated resveratrol, oligopeptide-1, niacinamide, *Opuntia ficus-indica* extract, *Prunus mume* extract, algae extract, malachite extract, adenosine, and/or *Opuntia tuna* fruit extract, or any combination thereof, or all of such active ingredients, or at least 1, 2, 3, 4, 5, 6, 7, 8, and/or 9 of such active ingredients. It should be recognized that other standard testing vehicles can also be used to determine the skin benefit properties of active ingredient and that the following formulations are non-limiting testing vehicles.

TABLE 6*

| Ingredient | % Concentration (by weight) |
|---|---|
| Phase A | |
| Water | 84.80 |
| Xanthan gum | 0.1 |

TABLE 6*-continued

| Ingredient | % Concentration (by weight) |
|---|---|
| M-paraben | 0.15 |
| P-paraben | 0.1 |
| Citric acid | 0.1 |
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |
| Phase C | |
| Active Ingredient** | 2.0 |
| TOTAL | 100 |

*Procedure for making composition: Sprinkle Xanthan gum in water and mix for 10 min. Subsequently, add all ingredients in phase A and heat to 70-75° C. Add all items in phase B to separate beaker and heat to 70-75° C. Mix phases A and B at 70-75° C. Continue mixing and allow composition to cool to 30° C. Subsequently, add phase C ingredient while mixing.
**The active ingredients identified throughout this specification can be incorporated into composition as the active ingredient. The active ingredients can be individually used or combined in this composition. The concentration ranges of the active ingredients (or combination of active ingredients) can be modified as desired or needed by increasing or decreasing the amount of water.

TABLE 7*

| Ingredient | % Concentration (by weight) |
|---|---|
| Phase A | |
| Water | 78.6 |
| M-paraben | 0.2 |
| P-paraben | 0.1 |
| Na$_2$ EDTA | 0.1 |
| Shea butter | 4.5 |
| Petrolatum | 4.5 |
| Glycerin | 4.0 |
| Propylene Glycol | 2.0 |
| Finsolve TN | 2.0 |
| Phase B | |
| Sepigel 305 | 2.0 |
| Phase C | |
| Active Ingredient** | 2.0 |
| TOTAL | 100 |

*Add ingredients in phase A to beaker and heat to 70-75° C. while mixing. Subsequently, add the phase B ingredient with phase A and cool to 30° C. with mixing. Subsequently, add phase C ingredient while mixing.
**The active ingredients identified throughout this specification can be incorporated into composition as the active ingredient. The active ingredients can be individually used or combined in this composition. The concentration ranges of the active ingredients (or combination of active ingredients) can be modified as desired or needed by increasing or decreasing the amount of water.

Example 3

The formulations represented in Table 8-13 are non-limiting examples of the types of formulations that can be prepared in the context of the present invention. Any standard method can be used to prepare such formulations. For instance, simple mixing of the ingredients in a beaker can be used. One should mix such ingredients and add heat as necessary to obtain a homogenous composition. The active ingredients that can be used in the formulations can include encapsulated resveratrol, oligopeptide-1, niacinamide, *Opuntia ficus-indica* extract, *Prunus mume* extract, algae extract, malachite extract, adenosine, and/or *Opuntia tuna* fruit extract, or any combination thereof, or all of such active ingredients, or at least 1, 2, 3, 4, 5, 6, 7, 8, and/or 9 of such active ingredients.

Table 8 includes a non-limiting example of a composition of the present invention. The composition can be formulated into an emulsion (e.g., o/w, w/o, o/w/o, w/o/w, etc.) and the additional ingredients identified throughout the specification can be included into the Table 8 composition (e.g., by adjusting the water content of composition). Further, the concentration ranges of the ingredients identified in Table 8 can vary depending on a desired formulation (e.g., cream, lotion, moisturizer cleanser, etc.).

TABLE 8

| Ingredient | % Concentration (by weight) |
|---|---|
| Water | q.s. |
| Active Ingredient* | 0.1% to 10% |
| Glycerin | 3 to 40% |
| Butylene glycol | 0.0001 to 10% |
| Propylene glycol | 0.0001 to 10% |
| Phenoxyethanol | 0.0001 to 10% |
| Disodium EDTA | 0.0001 to 10% |
| Steareth-20 | 0.0001 to 10% |
| Chlorhexidine Diglunonate | 0.0001 to 10% |
| Potassium Sorbate | 0.0001 to 10% |
| Preservative** | 0.0001 to 2% |
| TOTAL | 100 |

*The active ingredients identified throughout this specification can be incorporated into composition as the active ingredient. The active ingredients can be individually used or combined in this composition. The concentration ranges of the active ingredients (or combination of active ingredients) can be modified as desired or needed by increasing or decreasing the amount of water.
**Any preservative can be used identified in the specification or those known in the art.

Table 9 includes a non-limiting example of a composition of the present invention. The composition can be formulated into an emulsion (e.g., o/w, w/o, o/w/o, w/o/w, etc.) and the additional ingredients identified throughout the specification can be included into the Table 9 composition (e.g., by adjusting the water content of composition). Further, the concentration ranges of the ingredients identified in Table 9 can vary depending on a desired formulation (e.g., cream, lotion, moisturizer cleanser, etc.).

TABLE 9

| Ingredient | % Concentration (by weight) |
|---|---|
| Water | q.s. |
| Active Ingredient* | 0.1% to 10% |
| Dimethicone | 0.0001 to 10% |
| Triethanolamine | 0.0001 to 10% |
| Phenonip | 0.0001 to 10% |
| Betaine | 0.0001 to 10% |
| Disodium EDTA | 0.0001 to 10% |
| Tocopheryl acetate | 0.0001 to 10% |
| Prodew 400 | 0.0001 to 10% |
| Preservative** | 0.0001 to 2% |
| TOTAL | 100 |

*The active ingredients identified throughout this specification can be incorporated into composition as the active ingredient. The active ingredients can be individually used or combined in this composition. The concentration ranges of the active ingredients (or combination of active ingredients) can be modified as desired or needed by increasing or decreasing the amount of water.
**Any preservative can be used identified in the specification or those known in the art.

Table 10 includes a non-limiting example of a composition of the present invention. The composition can be formulated into an emulsion (e.g., o/w, w/o, o/w/o, w/o/w, etc.) and the additional ingredients identified throughout the specification can be included into the Table 10 composition (e.g., by adjusting the water content of composition). Further, the concentration ranges of the ingredients identified in Table 10 can vary depending on a desired formulation (e.g., cream, lotion, moisturizer cleanser, etc.). In particular embodiments, the Table 10 composition can be a moisturizer.

TABLE 10

| Ingredient | % Concentration (by weight) |
| --- | --- |
| Water | q.s. |
| Active Ingredient* | 0.1% to 10% |
| Glycerin | 0.0001 to 10% |
| Pentylene Glycol | 0.0001 to 10% |
| Capryl Glycol | 0.0001 to 10% |
| Disodium EDTA | 0.0001 to 10% |
| Capric/Caprylic Triglyceride | 0.0001 to 10% |
| Lipex 205 (Shea Butter) | 0.0001 to 10% |
| Squalane | 0.0001 to 10% |
| Cetyl Alcohol | 0.0001 to 10% |
| Dimethicone | 0.0001 to 10% |
| Ceramide II | 0.0001 to 10% |
| Stearic Acid | 0.0001 to 10% |
| Super Sterol Ester | 0.0001 to 10% |
| Arlacel 165 | 0.0001 to 10% |
| Simulgel 600 | 0.0001 to 10% |
| TOTAL | 100 |

*The active ingredients identified throughout this specification can be incorporated into composition as the active ingredient. The active ingredients can be individually used or combined in this composition. The concentration ranges of the active ingredients (or combination of active ingredients) can be modified as desired or needed by increasing or decreasing the amount of water.

Table 11 includes a non-limiting example of a composition of the present invention. The composition can be formulated into an emulsion (e.g., o/w, w/o, o/w/o, w/o/w, etc.) and the additional ingredients identified throughout the specification can be included into the Table 11 composition (e.g., by adjusting the water content of composition). Further, the concentration ranges of the ingredients identified in Table 11 can vary depending on a desired formulation (e.g., cream, lotion, moisturizer cleanser, etc.). In particular embodiments, the Table 11 composition can be a moisturizer.

TABLE 11

| Ingredient | % Concentration (by weight) |
| --- | --- |
| Water | q.s. |
| Active Ingredient* | 0.1% to 10% |
| Glycerin | 0.0001 to 10% |
| Pentylene Glycol | 0.0001 to 10% |
| Capryl Glycol | 0.0001 to 10% |
| Disodium EDTA | 0.0001 to 10% |
| Petrolatum | 0.0001 to 10% |
| Squalane | 0.0001 to 10% |
| Cetyl Alcohol | 0.0001 to 10% |
| Arlacel 165 | 0.0001 to 10% |
| Dimethicone | 0.0001 to 10% |
| Simulgel 600 | 0.0001 to 10% |
| TOTAL | 100 |

*The active ingredients identified throughout this specification can be incorporated into composition as the active ingredient. The active ingredients can be individually used or combined in this composition. The concentration ranges of the active ingredients (or combination of active ingredients) can be modified as desired or needed by increasing or decreasing the amount of water.

Table 12 includes a non-limiting example of a composition of the present invention. The composition can be formulated into an emulsion (e.g., o/w, w/o, o/w/o, w/o/w, etc.) and the additional ingredients identified throughout the specification can be included into the Table 12 composition (e.g., by adjusting the water content of composition). Further, the concentration ranges of the ingredients identified in Table 12 can vary depending on a desired formulation (e.g., cream, lotion, moisturizer cleanser, etc.). In particular embodiments, the Table 12 composition can be a sunscreen lotion.

TABLE 12

| Ingredient | % Concentration (by weight) |
| --- | --- |
| Water | q.s. |
| Active Ingredient* | 0.1% to 10% |
| Xanthan Gum | 0.0001 to 10% |
| Disodium EDTA | 0.0001 to 10% |
| Pentylene Glycol | 0.0001 to 10% |
| Capryl Glycol | 0.0001 to 10% |
| Pemulen TR-1 | 0.0001 to 10% |
| Triethanolamine | 0.0001 to 10% |
| PVP/Hexadecene Copolymer | 0.0001 to 10% |
| Finsolv TN | 10 to 30% |
| Sorbitan Isostearate | 0.0001 to 10% |
| Sunscreen Ingredient** | 2 to 25% |
| TOTAL | 100 |

*The active ingredients identified throughout this specification can be incorporated into composition as the active ingredient. The active ingredients can be individually used or combined in this composition. The concentration ranges of the active ingredients (or combination of active ingredients) can be modified as desired or needed by increasing or decreasing the amount of water.
**Sunscreen ingredient can be any sunscreen ingredient, or combination of such ingredients, identified in the specification (e.g. UV absorbing and/or reflecting agents) or known to those of ordinary skill in the art. In one embodiment, the sunscreen ingredient is a combination of zinc oxide and titanium dioxide.

Table 13 includes a non-limiting example of a composition of the present invention. The additional ingredients identified throughout the specification can be included into the Table 13 composition (e.g., by adjusting the water content of composition). Further, the concentration ranges of the ingredients identified in Table 13 can vary depending on a desired formulation (e.g., cream, lotion, moisturizer cleanser, etc.). In particular embodiments, the Table 13 composition can be a cleanser.

TABLE 13

| Ingredient | % Concentration (by weight) |
| --- | --- |
| Water | q.s. |
| Active Ingredient* | 0.1% to 10% |
| Disodium EDTA | 0.0001 to 10% |
| Citric Acid | 0.0001 to 10% |
| Pentylene Glycol | 0.0001 to 10% |
| Capryl Glycol | 0.0001 to 10% |
| sodium methyl cocoyl taurate | 10 to 30% |
| sodium cocoamphodiacetate | 1 to 10% |
| TOTAL | 100 |

*The active ingredients identified throughout this specification can be incorporated into composition as the active ingredient. The active ingredients can be individually used or combined in this composition. The concentration ranges of the active ingredients (or combination of active ingredients) can be modified as desired or needed by increasing or decreasing the amount of water.

Example 4

Formulations having combinations of active ingredients disclosed herein from Example 1 were prepared as topical skin and/or hair compositions. The formulation in Table 14 was prepared as an eye cream. The formulation in Table 15 was prepared as a day cream. The formulations in Tables 16 and 17 were prepared as night creams. The formulations in Tables 18 and 19 were prepared as cleansers.

TABLE 14*

| Ingredient | % Concentration (by weight) |
| --- | --- |
| Water | 81 |
| Cetyl Alcohol | 3 |
| Glycerin | 3 |
| Cl2-15 Alkyl Benzoate | 3 |
| Stearic Acid | 2 |

TABLE 14*-continued

| Ingredient | % Concentration (by weight) |
|---|---|
| Glyceryl Stearate | 2 |
| PEG-100 Stearate | 1 |
| 1,2-Hexanediol | 1 |
| Niacinamide | 1 |
| Triethanolamine | 0.6 |
| Benzyl Alcohol | 0.5 |
| Ethylhexyl Palmitate | 0.5 |
| Silica | 0.5 |
| Mica | 0.3 |
| Titanium Dioxide | 0.2 |
| Xanthan Gum | 0.2 |
| Dimethicone | 0.2 |
| Dipotassium Glycyrrhizate | 0.1 |
| Disodium EDTA | 0.1 |
| Algae Extract | 0.06 |
| Resveratrol | 0.003 |
| Oligopeptide-1 | 0.00006 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients can be added, for example, to modify the rheological properties of the composition. Alternatively, the amount of water can be varied so long as the amount of water in the composition is at least 35% w/w, and preferably between 70 to 90% w/w.

TABLE 15*

| Ingredient | % Concentration (by weight) |
|---|---|
| Water | 53 |
| Homosalate | 9 |
| Glycerin | 8 |
| Ethylhexyl Salicylate (Octisalate) | 5 |
| Oxybenzone | 5 |
| Avobenzone | 3 |
| Octocrylene | 3 |
| Dicaprylyl Carbonate | 2 |
| Cetearyl Alcohol | 2 |
| Dimethicone | 2 |
| Ammonium Acryloyldimethyltaurate/VP Copolymer | 2 |
| Ceteareth-25 | 1 |
| Niacinamide | 1 |
| Opuntia Ficus-Indica Fruit Extract | 1 |
| Phenoxyethanol | 0.7 |
| Disodium Ethylene Dicocamide PEG-15 Disulfate | 0.5 |
| Hydroxyacetophenone | 0.5 |
| Jojoba Esters (optional) | 0.5 |
| Behenyl Alcohol (optional) | 0.3 |
| Silica | 0.3 |
| Methyldihydrojasmonate | 0.3 |
| Ethylene Brassylate | 0.2 |
| Bisabolol | 0.2 |
| Caprylyl Glycol | 0.2 |
| Disodium EDTA | 0.2 |
| Decylene Glycol | 0.1 |
| Tocopheryl Acetate | 0.1 |
| Adenosine (optional) | 0.04 |
| Malachite Extract (optional) | 0.003 |
| Resveratrol | 0.003 |
| Opuntia Tuna Fruit Extract (optional) | 0.0005 |
| Oligopeptide-1 | 0.00006 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients can be added, for example, to modify the rheological properties of the composition. Alternatively, the amount of water can be varied so long as the amount of water in the composition is at least 35% w/w, and preferably between 40 to 60% w/w.

TABLE 16*

| Ingredient | % Concentration (by weight) |
|---|---|
| Water | 66 |
| Isohexadecane | 7 |
| Glycerin | 5 |
| Dimethicone | 4 |
| Pentylene Glycol | 4 |
| Aluminum Starch Octenyl succinate | 3 |
| Cetearyl Alcohol | 2 |
| Glyceryl Stearate | 1 |
| Ammonium Acryloyldimethyltaurate/VP Copolymer | 1 |
| Ceteareth-33 | 1 |
| Isopropyl Palmitate | 1 |
| Niacinamide | 1 |
| Phenoxyethanol | 0.8 |
| Butylene Glycol | 0.6 |
| Caprylic/Capric Triglyceride | 0.5 |
| Prunus Mume Leaf Extract | 0.4 |
| Acrylamide/Sodium Acryloyldimethyltaurate Copolymer | 0.3 |
| Panthenol | 0.3 |
| Methyldihydrojasmonate | 0.1 |
| Ethylene Brassylate | 0.1 |
| Dipotassium Glycyrrhizate | 0.1 |
| Disodium EDTA | 0.05 |
| Adenosine (optional) | 0.04 |
| Malachite Extract (optional) | 0.003 |
| Resveratrol | 0.003 |
| Opuntia Tuna Fruit Extract (optional) | 0.0005 |
| Oligopeptide-1 | 0.00006 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients can be added, for example, to modify the rheological properties of the composition. Alternatively, the amount of water can be varied so long as the amount of water in the composition is at least 35% w/w, and preferably between 50 to 80% w/w.

TABLE 17*

| Ingredient | % Concentration (by weight) |
|---|---|
| Water | 72 |
| Glycerin | 5 |
| Isohexadecane | 4 |
| Butylene Glycol | 3 |
| Aluminum Starch Octenyl succinate | 2 |
| Isocetyl Stearate | 2 |
| Cetyl Alcohol | 2 |
| Cetyl Esters | 2 |
| Caprylyl Methicone | 1 |
| Niacinamide | 1 |
| Phenoxyethanol | 0.7 |
| Cetearyl Alcohol | 0.6 |
| Glyceryl Stearate | 0.6 |
| Acrylamide/Sodium Acryloyldimethyltaurate Copolymer | 0.6 |
| Caprylic/Capric Triglyceride | 0.5 |
| Hydroxyacetophenone | 0.5 |
| Stearic Acid | 0.5 |
| PEG-100 Stearate | 0.4 |
| Prunus Mume Leaf Extract | 0.4 |
| Arachidyl Alcohol | 0.3 |
| Triethanolamine | 0.3 |
| Dimethicone | 0.2 |
| Ceteareth-20 | 0.2 |
| Caprylyl Glycol | 0.2 |
| Behenyl Alcohol | 0.2 |
| Titanium Dioxide | 0.2 |
| Decylene Glycol | 0.1 |
| Methyldihydrojasmonate | 0.1 |
| Tocopheryl Acetate | 0.1 |
| Polysorbate 80 | 0.1 |

TABLE 17*-continued

| Ingredient | % Concentration (by weight) |
| --- | --- |
| Ethylene Brassylate | 0.1 |
| Acrylates/C10-13 Alkyl Acrylate Crosspolymer | 0.1 |
| Disodium EDTA | 0.1 |
| Adenosine (optional) | 0.04 |
| Malachite Extract (optional) | 0.003 |
| Resveratrol | 0.003 |
| *Opuntia Tuna* Fruit Extract (optional) | 0.0005 |
| Oligopeptide-1 | 0.00006 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients can be added, for example, to modify the rheological properties of the composition. Alternatively, the amount of water can be varied so long as the amount of water in the composition is at least 35% w/w, and preferably between 55 to 85% w/w.

TABLE 18*

| Ingredient | % Concentration (by weight) |
| --- | --- |
| Water | 67 |
| Cetearyl Alcohol | 4 |
| Sodium Stearoyl Glutamate | 4 |
| Sodium Cocoyl Glutamate | 3 |
| Acrylates Copolymer | 3 |
| Cocamidopropyl Betaine | 3 |
| Propanediol | 3 |
| PPG-2 Hydroxyethyl Coco/Isostearamide | 3 |
| Glycerin | 2 |
| Hydrolyzed Corn Starch | 2 |
| Sodium Laureth Sulfate | 1 |
| Potassium Hydroxide | 1 |
| Magnesium Aluminum Silicate | 1 |
| Coco-glucoside | 0.7 |
| Methyldihydrojasmonate | 0.3 |
| Ethylene Brassylate | 0.3 |
| Sodium Chloride | 0.3 |
| *Copernicia Cerifera* (Carnauba) Wax/Cire De Carnauba | 0.2 |
| Citric Acid | 0.2 |
| Disodium EDTA | 0.2 |
| Titanium Dioxide | 0.2 |
| Lactose | 0.1 |
| Hydroxypropyl Cyclodextrin | 0.1 |
| Tetramethyl Acetyloctahydronaphthalenes | 0.1 |
| Niacinamide | 0.01 |
| Malachite Extract (optional) | 0.0003 |
| Resveratrol | 0.0003 |
| *Opuntia Tuna* Fruit Extract (optional) | 0.0001 |
| Oligopeptide-1 | 0.000002 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients can be added, for example, to modify the rheological properties of the composition. Alternatively, the amount of water can be varied so long as the amount of water in the composition is at least 35% w/w, and preferably between 50 to 80% w/w.

TABLE 19*

| Ingredient | % Concentration (by weight) |
| --- | --- |
| Water | 75 |
| TEA-Lauryl Sulfate | 10 |
| Acrylates Copolymer | 3 |
| Propanediol | 3 |
| Cocamidopropyl Betaine | 2 |
| Triethanolamine | 2 |
| PPG-2 Hydroxyethyl Coco/Isostearamide | 2 |
| *Copernicia Cerifera* (Carnauba) Wax/Cire De Carnaube | 0.2 |
| Sodium Chloride | 0.2 |

TABLE 19*-continued

| Ingredient | % Concentration (by weight) |
| --- | --- |
| Disodium EDTA | 0.2 |
| Lactose | 0.1 |
| Hydroxypropyl Cyclodextrin | 0.1 |
| Glycerine | 0.03 or 0.007 |
| Niacinamide | 0.01 |
| Resveratrol | 0.003 |
| *Opuntia Tuna* Fruit Extract (optional) | 0.0005 |
| Malachite Extract (optional) | 0.0003 |
| Oligopeptide-1 | 0.000002 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients can be added, for example, to modify the rheological properties of the composition. Alternatively, the amount of water can be varied so long as the amount of water in the composition is at least 35% w/w, and preferably between 65 to 85% w/w.

Example 5

In Vitro Efficacy of Ingredients

The efficacy of the ingredients were determined by the following methods. The following are non-limiting assays that can be used in the context of the present invention. It should be recognized that other testing procedures can be used, including, for example, objective and subjective procedures.

It was determined that oligopeptide 1 inhibits tyrosinase, increases elastin production, increases collagen stimulation, and inhibits TNF-α. It was also determined that niacinamide inhibits melanogenesis in B16 cells. It was determined that *Opuntia ficus-indica* extract inhibits COX-1 and COX-2, inhibits lipoxygenase, and inhibits TNF-α. It was also determined that malachite extract inhibits MMP1, inhibits COX-1 and COX-2, inhibits lipoxygenase, and possesses antioxidant properties. It was determined that *Prunus mume* extract possesses antioxidant properties, increases collagen stimulation, and increases laminin production. It was also determined that algae extract reduces keratinocyte monolayer permeability. A summary of quantitative results is found in Table 20 and the methods used to determine the properties of the ingredients are provided below.

TABLE 20

| Assay | Ingredient | Activity |
| --- | --- | --- |
| Inhibition of MMP1 | Malachite extract | −60% |
| Inhibition of COX-1 | *Opuntia ficus-indica* extract | −65% |
|  | Malachite extract | −47% |
| Inhibition of COX-2 | *Opuntia ficus-indica* extract | −73% |
|  | Malachite extract | −37% |
| Inhibition of Lipoxygenase | *Opuntia ficus-indica* extract | −63% |
|  | Malachite extract | −26% |
| Inhibition of Tyrosinase | Oligopeptide-1 | −40% |
| Inhibition of Melanogenesis | Niacinamide | −30% |
| Elastin Production | Oligopeptide-1 | +23% |
| Collagen Stimulation | Oligopeptide-1 | +20% |
|  | *Prunus mume* extract | +71% |
| Laminin Production | *Prunus mume* extract | +57% |
| Inhibition of TNF-α | Oligopeptide-1 | −40% |
|  | *Opuntia ficus-indica* extract | −50% |

TABLE 20-continued

| Assay | Ingredient | Activity |
| --- | --- | --- |
| Antioxidant Capacity | Malachite extract | +29% |
| | *Prunus mume* extract | +89% |
| | Resveratrol | +100% |
| Keratinocyte Monolayer Permeability | Algae extract | −45% |

Inhibition of Matrix Metalloproteinase 1 Enzyme (MMP1)—

Malachite extract has been shown to inhibit MMP1. MMPs are extracellular proteases that play a role in many normal and disease states by virtue of their broad substrate specificity. MMP1 substrates include collagen IV. The activity of MMP1 in the presence or absence of malachite extract was determined using the Molecular Probes Enz/Chek Gelatinase/Collagenase Assay kit (#E12055). It was determined that malachite extract inhibits MMP1 activity by 60%.

Briefly, this kit utilizes a fluorogenic gelatin substrate to detect MMP1 protease activity in vitro. Upon proteolytic cleavage of the fluorogenic gelatin substrate, bright green fluorescence was revealed and was monitored using a fluorescent microplate reader to measure enzymatic activity. Test materials or control reagents were incubated in the presence or absence of the purified enzyme and substrate to determine their protease inhibitor capacity.

Cyclooxygenase 1 (COX-1) and Cyclooxygenase 2 (COX-2) Assay—

*Opuntia ficus-indica* extract and malachite extract have been shown to inhibit COX-1 and COX-2. These enzymes contribute to the inflammatory pathway. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. The peroxidase activity of COX-1 and COX-2 was determined in the presence or absence of *Opuntia ficus-indica* extract or malachite extract using the Colorimetric COX (ovine) Inhibitor screening assay (#760111, Cayman Chemical). It was determined that *Opuntia ficus-indica* extract inhibited COX-1 activity by 65% and COX-2 by 73% and malachite extract inhibited COX-1 activity by 47% and COX-2 activity by 37%.

COX-1 and COX-2 peroxidase activity was assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. According to manufacturer instructions and purified enzyme and heme with or without test extracts were mixed in assay buffer and incubated with shaking for 15 min at room temperature. Following incubation, arachidonic acid and colorimetric substrate were added to initiate the reaction. Color progression was evaluated by colorimetric plate reading at 590 nm. The percent inhibition of COX-1 or COX-2 activity was calculated and compared to non-treated controls to determine the ability of test extracts to inhibit the activity of the purified enzymes.

Lipoxygenase (LO) Assay—

*Opuntia ficus-indica* extract and malachite extract have been shown to inhibit LO activity. LO contributes to the inflammatory pathway. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotrienes, potent inflammatory mediators. The activity of LO was determined in the presence or absence of *Opuntia ficus-indica* extract or malachite extract, using the Colorimetric LO Inhibitor screening kit (#760700, Cayman Chemical). It was determined that *Opuntia ficus-indica* extract inhibits LO activity by 63% and malachite extract inhibits LO activity by 26%.

LO activity was assayed by an accurate and convenient method for screening lipoxygenase inhibitors by measuring the hydroperoxides generated from the incubation of a lipoxygenase (5-, 12-, or 15-LO) with arachidonic acid. Purified 15-lipoxygenase with and without the test ingredients was mixed in assay buffer and incubated with shaking for 10 min at room temperature. Following incubation, arachidonic acid was added to initiate the reaction and the mixtures were incubated for an additional 10 min at room temperature. Colorimetric substrate was added to terminate catalysis and color progression was evaluated by fluorescence plate reading at 490 nm. The percent inhibition of lipoxygenase activity was calculated compared to non-treated controls to determine the ability of each test ingredient to inhibit the activity of purified enzyme.

Mushroom Tyrosinase Activity Assay—

Oligopeptide-1 was shown to inhibit tyrosinase activity. In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. The activity of tyrosinase on its substrate L-Dopa in the presence or absence of oligopeptide-1 was determined using a colorimetric mushroom tyrosinase activity assay. It was determined that oligopeptide-1 inhibits tyrosinase by 40%.

Tyrosinase activity was assayed by measuring the ability of purified mushroom tyrosinase (Sigma) to oxidize its substrate, L-Dopa (Fisher), in the presence or absence of oligopeptide-1. Oxidation of L-DOPA by the tyrosinase produced a pigment that was evaluated by colorimetric plate reading at 490 nm. The percent inhibition of mushroom tyrosinase activity was calculated and compared to non-treated controls to determine the ability of test ingredients to inhibit the activity of purified enzyme. Test inhibition was compared with that of the known tyrosinase inhibitor kojic acid (Sigma).

B16 Pigmentation Assay—

Niacinamide was shown to inhibit melanogenesis.

Melanogenesis is the process by which melanocytes produce melanin, a naturally produced pigment that imparts color to skin, hair, and eyes. Inhibiting melanogenesis is beneficial to prevent skin darkening and lighten dark spots associated with aging. Melanogenesis in B16 cells was determined in the presence or absence of niacinamide by measuring melanin secretion. It was determined that niacinamide inhibits melanogenesis by 30%.

Melanogenesis was determined using B16-F1 melanocytes (ATCC), an immortalized mouse melanoma cell line. The endpoint of this assay was a spectrophotometric measurement of melanin production and cellular viability. B16-F1 melanocytes, were cultivated in standard DMEM growth medium with 10% fetal bovine serum (Mediatech) at 37° C. in 10% $CO_2$ and then treated with or without niacinamide for 6 days. Following incubation, melanin secretion was measured by absorbance at 405 nm and cellular viability was quantified.

Elastin Stimulation Assay—

Oligopeptide-1 has been shown to increase elastin production. Elastin is a connective tissue protein that helps skin resume shape after stretching or contracting. Elastin is also an important load-bearing protein used in places where mechanical energy is required to be stored. Elastin is made by linking many soluble tropoelastin protein molecules, in a reaction catalyzed by lysyl oxidase. Elastin production was determined in cultured human fibroblasts incubated in the presence or absence of oligopeptide-1. It was determined that oligopeptide-1 increased elastin production by 23%.

Elastin secretion and elastin fibers were monitored by staining of cultured human fibroblasts using antibodies directed against elastin. Human fibroblasts were treated with or without oligopeptide-1. Following incubation, elastin content was measured using immunofluorescent antibodies directed against elastin.

Collagen Stimulation Assay—

Oligopeptide-1 and *Prunus mume* extract have been shown to increase collagen stimulation. Collagen is an extracellular matrix protein critical for skin structure. Increased synthesis of collagen helps improve skin firmness and elasticity. Collagen stimulation was determined using a sandwich enzyme linked immuno-sorbant assay (ELISA) from Takara (#MK101) by measuring production of procollagen peptide (a precursor to collagen) in human epidermal fibroblasts incubated in the presence or absence of oligopeptide-1 or *Prunus mume* extract. It was determined that oligopeptide-1 increased collagen stimulation by 20% and *Prunus mume* extract increased collagen stimulation by 71%.

Collagen stimulation can be monitored by a spectrophotometric measurement that reflects the presence of procollagen peptide and cellular viability. The assay employs the quantitative sandwich enzyme immunoassay technique whereby a monoclonal antibody specific for procollagen peptide has been pre-coated onto microplate wells. Subconfluent normal human adult epidermal fibroblasts (Cascade Biologics) cultivated in standard DMEM growth medium with 10% fetal bovine serum (Mediatech) at 37° C. in 10% $CO_2$, were treated with or without oligopeptide-1 or *Prunus mume* extract for 3 days. Following incubation, cell culture medium was collected (samples and controls) and the amount of procollagen peptide secretion was quantified using a sandwich enzyme linked immuno-sorbant assay (ELISA) from Takara (#MK101). Standards, controls and/or samples were pipetted into the wells precoated with anti-procollagen peptide antibody and the procollagen peptide present was allowed to be bound by the immobilized antibody. After washing away any unbound substances, an enzyme-linked polyclonal antibody specific for procollagen peptide was added to the wells. Following a wash to remove any unbound antibody-enzyme reagent, a substrate solution was added to the wells that allowed color development in proportion to the amount of procollagen peptide bound in the initial step. The color development was stopped and the color development was measured at 450 nm by a microplate reader.

Laminin Stimulation Assay—

*Prunus mume* extract has been shown to increase laminin production. Laminin and fibronectin are major proteins in the dermal-epidermal junction (DEJ) (also referred to as the basement membrane). The DEJ is located between the dermis and the epidermis interlocks forming fingerlike projections called rete ridges. The cells of the epidermis receive their nutrients from the blood vessels in the dermis. The rete ridges increase the surface area of the epidermis that is exposed to these blood vessels and the needed nutrients. The DEJ provides adhesion of the two tissue compartments and governs the structural integrity of the skin. Laminin and fibronectin are two structural glycoproteins located in the DEJ. Considered the glue that holds the cells together, laminin and fibronectin are secreted by dermal fibroblasts to help facilitate intra- and inter-cellular adhesion of the epidermal calls to the DEJ. Laminin secretion was monitored in cultured human fibroblasts using immunofluorescent antibodies directed against laminin in an enzyme linked immuno-sorbant assay (ELISA). It was determined that *Prunus mume* extract increased laminin secretion by 57%.

Laminin secretion was monitored by quantifying laminin in cell supernatants of cultured human fibroblasts treated for 3 days with culture medium with or without 1.0% final concentration of *Prunus mume* extract. Following incubation, laminin content was measured using immunofluorescent antibodies directed against laminin in an enzyme linked immuno-sorbant assay (ELISA). Measurements were normalized for cellular metabolic activity, as determined by bioconversion of 3-(4,5-dimethylthiazol-2-yl)-5-(3-carboxymethoxyphenyl)-2-(4-sulfophenyl)-2H-tetrazolium (MTS).

Inhibition of Tumor Necrosis Factor Alpha (TNF-α)—

Oligopeptide-1 and *Opuntia ficus-indica* extract have been shown to inhibit TNF-α production in keratinocytes. TNF-α is the prototype ligand of the TNF superfamily. It is a pleiotropic cytokine that plays a central role in inflammation. Increase in its expression is associated with an up regulation in pro-inflammatory activity. The bioassay used to analyze the effect of oligopeptide-1 and *Opuntia ficus-indica* extract used a spectrophotometric measurement that reflects the presence of TNF-α and cellular viability. It was determined that oligopeptide-1 and *Opuntia ficus-indica* extract inhibits TNF-α production in keratinocytes by 40% and 50%.

Subconfluent normal human adult keratinocytes (Cascade Biologics) cultivated in EpiLife standard growth medium (Cascade Biologics) at 37° C. in 5% CO2, were treated with phorbol 12-myristate 13-acetate (PMA, 10 ng/ml, Sigma Chemical, #P1585-1MG) and either oligopeptide-1 or *Opuntia ficus-indica* extract (treated samples) or no additional treatment (untreated sample) for 6 hours. PMA causes a dramatic increase in TNF-α secretion which peaks at 6 hours after treatment. Following incubation, cell culture medium was collected and the amount of TNF-a secretion quantified using a sandwich enzyme linked immuno-sorbant assay (ELISA) from R&D Systems (#DTA00C).

Briefly, the ELISA assay employed the quantitative sandwich enzyme immunoassay technique whereby a monoclonal antibody specific for TNF-α was been pre-coated onto a microplate. Standards and treated and untreated samples were pipetted into the microplate wells to allow any TNF-α present to be bound by the immobilized antibody. After washing away any unbound substances, an enzyme-linked polyclonal antibody specific for TNF-α was added to the wells. Following a wash to remove any unbound antibody-enzyme reagent, a substrate solution was added to the wells to allow color development in proportion to the amount of TNF-α bound in the initial step. The color development was stopped at a specific time and the intensity of the color at 450 nm was measured using a microplate reader.

Antioxidant Capacity—

Malachite extract, *Prunus mume* extract, and resveratrol have been shown to possess antioxidant capacity. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it accounts for the cumulative effect of all antioxidants present in plasma and body fluids. It was determined that malachite extract, *Prunus mume* extract, and resveratrol possess an antioxidant capacity of 29%, 89%, and 100% of trolox, respectively. These antioxidant capacities indicate that malachite extract and *Prunus mume* extract is capable of reducing oxidizing agents (oxidants).

Antioxidant capacity was determined by an Oxygen Radical Absorption (or Absorbance) Capacity (ORAC) assay. This assay quantifies the degree and length of time it takes to inhibit the action of an oxidizing agent, such as oxygen radicals, that are known to cause damage to cells (e.g., skin cells). The ORAC value of control, malachite extract, *Prunus mume* extract, and resveratrol was determined by the Zen-Bio ORAC Anti-oxidant Assay kit (#AOX-2). Briefly, this assay measures the loss of fluorescein fluorescence over time due to the peroxyl-radical formation by the breakdown of AAPH (2,2'-axobis-2-methyl propanimidamide, dihydrochloride). Trolox, a water soluble vitamin E analog, serves as positive antioxidant control that inhibits fluorescein decay in a dose dependent manner.

Decreases Keratinocyte Monolayer Permeability—

Algae extract has been shown to decrease keratinocyte monolayer permeability. This is a measure of skin barrier integrity. Keratinocyte monolayer permeability in treated and non-treated keratinocytes were determined using the In Vitro Vascular Permeability assay by Millipore (ECM642). This assay analyzes endothelial cell adsorption, transport and permeability. It was determined that algae extract decreases keratinocyte monolayer permeability by 45%.

Samples were tested according to the In Vitro Vascular Permeability assay manufacturer's instructions. Briefly, adult human epidermal keratinocytes from Life Technologies (C-005-5C) were seeded onto a porous collagen-coated membrane within a collection well. The keratinocytes were incubated in Epilife growth media with calcium from Life Technologies (M-EP-500-CA) supplemented with Keratinocyte Growth Supplement (HKGS) from Life Technologies (S-101-5) for 24 hours at 37° C. and 5% $CO_2$. This incubation time allowed the cells to form a monolayer and occlude the membrane pores. The media was then replaced with fresh media with (test sample)/without (non-treated control) test compounds/extracts and the keratinocytes were incubated for an additional 48 hours at 37° C. and 5% $CO_2$. To determine permeability of the keratinocyte monolayer after incubation with/without the test compound/extract, the media was replaced with fresh media containing a high molecular weight Fluorescein isothiocyanate (FITC)-Dextran and the keratinocytes are incubated for 4 hours at 37° C. and 5% $CO_2$. During the 4 hours incubation, FITC passed through the keratinocytes monolayer and porous membrane into the collection well at a rate proportional to the monolayer's permeability. After the 4 hour incubation, cell viability and the content of FITC in the collection wells was determined. For the FITC content, the media in the collection well was collected and fluorescence of the media determined at 480 nm (Em) when excited at 520 nm. Percent permeability and percent change in comparison to the non-treated controls were determined by the following equations: Percent Permeability=((Mean Ex/Em of test sample)/Mean Ex/Em untreated control)*100; Percent Change=Percent Permeability of test sample−Percent Permeability of untreated control.

Example 6

Clinical Efficacy of Compositions

The compositions described in Tables 14 through 19 have been shown to: improve the appearance of fine lines, wrinkles, texture/smoothness, overall appearance, and increase elasticity and radiance/luminosity. The objective of this study was to assess the effectiveness of use of a regimen of either the compositions of Tables 14, 15, 16, and 18 or compositions of Tables 14, 15, 17, and 19 on the ability to improve the appearance of facial and neck skin. The study assessed the skin through expert clinical grading. It was determined that both regimens statistically significantly improve the appearance of skin fine lines (sub-orbital), fine lines (global), wrinkles (global), radiance/luminosity, texture/smoothness (visual), texture/smoothness (tactile), elasticity (tactile) and overall appearance after four, eight, and twelve weeks of test regimen use, as well as skin tone (clarity), tone (evenness) and firmness (visual) after eight and twelve weeks and wrinkles (sub-orbital) after twelve weeks.

Briefly, 62 human subjects, aged 25 to 45 years (average age 37.6±5.3) with presence of early signs of facial skin aging participated in a 12 week, monadic evaluation of the compositions of Tables 14 through 19 when used on the face, neck, and eye area. Subjects were pre-screened and assigned into one of the two regimen groups based on their skin type. Regimen use was divided approximately equally, with 34 subjects with combination/oily skin using the compositions of Tables 14, 15, 17, and 19 and 28 subjects with normal/dry skin using the compositions of Tables 14, 15, 16, and 18.

All subjects discontinued use of all facial treatment products approximately one week prior to the initial, baseline visit. At the baseline visit and at 4, 8, and 12 weeks of use of the compositions of Tables 14 through 19, expert evaluation of facial and neck fine lines (sub-orbital and global), wrinkles (sub-orbital and global), radiance/luminosity, texture/smoothness (visual and tactile), skin tone (clarity and evenness), firmness (visual), elasticity (tactile), and overall appearance were assessed. The mean expert clinical grader evaluations at 4, 8, and 12 weeks of use were compared to the baseline measurement and statistically analyzed to determine statistical significance (95% confidence level ($p<0.05$)).

Subjects were instructed to apply the assigned cleanser formulation of Table 18 or 19 to the face and neck twice a day (morning and evening); the day cream formulation of Table 15 to the face and neck in the morning; the assigned night cream formulation of Table 16 or 17 to the face and neck in the evening; and the eye cream formulation of Table 14 under and around the eye area twice a day (morning and evening).

A summary of quantitative results is found in Table 21 below.

TABLE 21

| Assessment | Time Point | Mean ± SD | Mean Percent Improvement From BL mean | Percent of Subjects Improvement From BL | P-Value TX v.s. BL |
|---|---|---|---|---|---|
| Fine Lines (Sub-Orbital) | Baseline | 3.68± | | | |
| | Week 4 | 3.14± | 11.60% | 71.0% | <0.001* |
| | Week 8 | 3.10± | 11.81% | 64.5% | <0.001* |
| | Week 12 | 2.74± | 21.61% | 80.6% | <0.001* |
| Fine Lines (Global) | Baseline | 3.40± | | | |
| | Week 4 | 3.17± | 2.63% | 64.5% | 0.038* |
| | Week 8 | 2.85± | 11.58% | 74.2% | <0.001* |
| | Week 12 | 2.38± | 26.57% | 85.5% | <0.001* |
| Wrinkles (Sub-Orbital) | Baseline | 2.39± | | | |
| | Week 4 | 2.29± | NI | 53.2% | 0.298 |
| | Week 8 | 2.27± | NI | 56.5% | 0.186 |
| | Week 12 | 1 88± | 12.21% | 69.4% | <0.001* |
| Wrinkles (Global) | Baseline | 3.01± | | | |
| | Week 4 | 2.72± | 0.90% | 59.7% | 0.009* |
| | Week 8 | 2.51± | 8.12% | 69.4% | <0.001* |
| | Week 12 | 2.12± | 22.69% | 77.4% | <0.001* |
| Radiance/ Luminosity | Baseline | 4.68± | | | |
| | Week 4 | 3.95± | 13.03% | 79.0% | <0.001* |
| | Week 8 | 3.04± | 32.51% | 95.2% | <0.001* |
| | Week 12 | 2.28± | 49.13% | 98.4% | <0.001* |
| Texture/ Smoothness (Visual) | Baseline | 5.13± | | | |
| | Week 4 | 4.59± | 7.85% | 72.6% | <0.001* |
| | Week 8 | 4.05± | 18.97% | 83.9% | <0.001* |
| | Week 12 | 2.92± | 42.05% | 100% | <0.001* |
| Texture/ Smoothness (Tactile) | Baseline | 3.87± | | | |
| | Week 4 | 2.99± | 17.75% | 77.4% | <0.001* |
| | Week 8 | 2.59± | 28.03% | 88.7% | <0.001* |
| | Week 12 | 2.28± | 36.78% | 95.2% | <0.001* |
| Skin Tone (Clarity) | Baseline | 4.17± | | | |
| | Week 4 | 4.10± | NI | 51.6% | 0.493 |
| | Week 8 | 3.79± | 5.34% | 62.9% | 0.006* |
| | Week 12 | 2.91± | 28.18% | 85.5% | <0.001* |
| Skin Tone (Evenness) | Baseline | 4.12± | | | |
| | Week 4 | 3.97± | 1.24% | 62.9% | 0.107 |
| | Week 8 | 3.65± | 9.12% | 72.6% | <0.001* |
| | Week 12 | 2.90± | 27.95% | 88.7% | <0.001* |
| Firmness (Visual) | Baseline | 3.15± | | | |
| | Week 4 | 3.00± | 2.29% | 53.2% | 0.096 |
| | Week 8 | 2.81± | 7.67% | 64.5% | 0.001* |
| | Week 12 | 2.30± | 24.19% | 88.7% | <0.001* |
| Elasticity (Tactile) | Baseline | 3.38± | | | |
| | Week 4 | 2.85± | 12.08% | 72.6% | <0.001* |
| | Week 8 | 2.73± | 15.31% | 74.2% | <0.001* |
| | Week 12 | 2.18± | 32.06% | 93.5% | <0.001* |
| Overall Appearance | Baseline | 4.22± | | | |
| | Week 4 | 3.65± | 12.54% | 85.5% | <0.001* |
| | Week 8 | 3.21± | 22.42% | 90.3% | <0.001* |
| | Week 12 | 2.51± | 39.23% | 95.2% | <0.001* |

NI = No Improvement
*Indicates a statistically significant improvement compared to baseline, p ≤ 0.05

In conclusion, the use of a regimen of the compositions of Tables 14 to 19 significantly improves overall skin appearance, decreases facial and neck fine lines (sub-orbital and global), decreases wrinkles (sub-orbital and global), improves radiance/luminosity, improves texture/smoothness (visual and tactile), improves skin tone (clarity and evenness), improves firmness (visual), and improves elasticity (tactile).

Example 7

Assays that can be Use to Test Compositions

Assays that can be used to determine the efficacy of any one of the ingredients or any combination of ingredients or compositions having said combination of ingredients disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

B16 Pigmentation Assay:

Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilizes B16-F1 melanocytes (ATCC), an immortalized mouse melanoma cell line, to analyze the effect of compounds on melanogenesis. The endpoint of this assay is a spectrophotometric measurement of melanin production and cellular viability. B16-F1 melanocytes, can be cultivated in standard DMEM growth medium with 10% fetal bovine serum (Mediatech) at 37° C. in 10% $CO_2$ and then treated with any one of the active ingredients, combination of ingredients, or compositions having said combinations disclosed in the specification for 6 days. Following incubation, melanin secretion is measured by absorbance at 405 nm and cellular viability is quantified.

Collagen Stimulation Assay:

Collagen is an extracellular matrix protein critical for skin structure. Increased synthesis of collagen helps improve skin firmness and elasticity. This bioassay can be used to examine the effect of any one of the active ingredients, combination of ingredients, or compositions having said combinations disclosed in the specification on the production of procollagen peptide (a precursor to collagen) by human epidermal fibroblasts. The endpoint of this assay is a spectrophotometric measurement that reflects the presence of procollagen peptide and cellular viability. The assay employs the quantitative sandwich enzyme immunoassay technique whereby a monoclonal antibody specific for procollagen peptide has been pre-coated onto a microplate. Standards and samples can be pipetted into the wells and any procollagen peptide present is bound by the immobilized antibody. After washing away any unbound substances, an enzyme-linked polyclonal antibody specific for procollagen peptide can be added to the wells. Following a wash to remove any unbound antibody-enzyme reagent, a substrate solution can be added to the wells and color develops in proportion to the amount of procollagen peptide bound in the initial step using a microplate reader for detection at 450 nm. The color development can be stopped and the intensity of the color can be measured. For generation of samples and controls, subconfluent normal human adult epidermal fibroblasts (Cascade Biologics) cultivated in standard DMEM growth medium with 10% fetal bovine serum (Mediatech) at 37° C. in 10% $CO_2$, can be treated with each of the combination of ingredients or compositions having said combinations disclosed in the specification for 3 days. Following incubation, cell culture medium can be collected and the amount of procollagen peptide secretion quantified using a sandwich enzyme linked immuno-sorbant assay (ELISA) from Takara (#MK101).

Elastin Stimulation Assay:

Elastin is a connective tissue protein that helps skin resume shape after stretching or contracting. Elastin is also an important load-bearing protein used in places where mechanical energy is required to be stored. Elastin is made by linking many soluble tropoelastin protein molecules, in a reaction catalyzed by lysyl oxidase. Elastin secretion and elastin fibers can be monitored in cultured human fibroblasts by staining of cultured human fibroblasts using immunofluorescent antibodies directed against elastin.

Laminin Stimulation Assay:

Laminin and fibronectin are major proteins in the dermal-epidermal junction (DEJ) (also referred to as the basement membrane). The DEJ is located between the dermis and the epidermis interlocks forming fingerlike projections called rete ridges. The cells of the epidermis receive their nutrients from the blood vessels in the dermis. The rete ridges increase the surface area of the epidermis that is exposed to these blood vessels and the needed nutrients. The DEJ provides adhesion of the two tissue compartments and governs the structural integrity of the skin. Laminin and fibronectin are two structural glycoproteins located in the DEJ. Considered the glue that holds the cells together, laminin and fibronectin are secreted by dermal fibroblasts to help facilitate intra- and inter-cellular adhesion of the epidermal calls to the DEJ. Laminin secretion can be monitored by quantifying laminin in cell supernatants of cultured human fibroblasts treated for 3 days with culture medium with or without 1.0% final concentration of the test ingredient(s). Following incubation, laminin content can be measured using immunofluorescent antibodies directed against laminin in an enzyme linked immuno-sorbant assay (ELISA). Measurements are normalized for cellular metabolic activity, as determined by bioconversion of 3-(4,5-dimethylthiazol-2-yl)-5-(3-carboxymethoxyphenyl)-2-(4-sulfophenyl)-2H-tetrazolium (MTS).

Tumor Necrosis Factor Alpha (TNF-α) Assay:

The prototype ligand of the TNF superfamily, TNF-α, is a pleiotropic cytokine that plays a central role in inflammation. Increase in its expression is associated with an up regulation in pro-inflammatory activity. This bioassay can be used to analyze the effect of any one of the active ingredients, combination of ingredients, or compositions having said combinations disclosed in the specification on the production of TNF-α by human epidermal keratinocytes. The endpoint of this assay can be a spectrophotometric measurement that reflects the presence of TNF-α and cellular viability. The assay employs the quantitative sandwich enzyme immunoassay technique whereby a monoclonal antibody specific for TNF-α has been pre-coated onto a microplate. Standards and samples can be pipetted into the wells and any TNF-α present is bound by the immobilized antibody. After washing away any unbound substances, an enzyme-linked polyclonal antibody specific for TNF-α can be added to the wells. Following a wash to remove any unbound antibody-enzyme reagent, a substrate solution can be added to the wells and color develops in proportion to the amount of TNF-α bound in the initial step using a microplate reader for detection at 450 nm. The color development can be stopped and the intensity of the color can be measured. Subconfluent normal human adult keratinocytes (Cascade Biologics) cultivated in EpiLife standard growth medium (Cascade Biologics) at 37° C. in 5% $CO_2$, can be treated with phorbol 12-myristate 13-acetate (PMA, 10 ng/ml, Sigma Chemical, #P1585-1MG) and any one of the active ingredients, combination of ingredients, or compositions having said combinations disclosed in the specification for 6 hours. PMA has been shown to cause a dramatic increase in TNF-α secretion which peaks at 6 hours after treatment. Following incubation, cell culture medium can be collected and the amount of TNF-a secretion quantified using a sandwich enzyme linked immuno-sorbant assay (ELISA) from R&D Systems (#DTA00C).

Antioxidant (AO) Assay:

An in vitro bioassay that measures the total anti-oxidant capacity of any one of the ingredients, combination of ingredients, or compositions having said combinations disclosed in the specification. The assay relies on the ability of antioxidants in the sample to inhibit the oxidation of ABTS® (2,2'-azino-di-[3-ethylbenzthiazoline sulphonate]) to ABTS®.-F by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS oxidation is compared with that of Trolox, a water-soluble tocopherol analogue, and is quantified as molar Trolox equivalents. Anti-Oxidant capacity kit #709001 from Cayman Chemical (Ann Arbor, Mich. USA) can be used as an in vitro bioassay to measure the total anti-oxidant capacity of each of any one of the active ingredients, combination of ingredients, or compositions having said combinations disclosed in the specification. The protocol can be followed according to manufacturer recommendations. The assay relied on antioxidants in the sample to inhibit the oxidation of ABTS® (2,2'-azino-di-[3-ethylbenzthiazoline sulphonate]) to ABTS®.+by metmyoglobin. The capacity of the antioxidants in the sample to prevent ABTS oxidation can be compared with that Trolox, a water-soluble tocopherol analogue, and can be quantified as a molar Trolox equivalent.

ORAC Assay:

Oxygen Radical Absorption (or Absorbance) Capacity (ORAC) of any one of the active ingredients, combination of ingredients, or compositions having said combinations disclosed in the specification can also be assayed by measuring the antioxidant activity of such ingredients or compositions. Antioxidant activity indicates a capability to reduce oxidizing agents (oxidants). This assay quantifies the degree and length of time it takes to inhibit the action of an oxidizing agent, such as oxygen radicals, that are known to cause damage to cells (e.g., skin cells). The ORAC value of any one of the active ingredients, combination of ingredients, or compositions having said combinations disclosed in the specification can be determined by methods known to those of ordinary skill in the art (see U.S. Publication Nos. 2004/0109905 and 2005/0163880; and commercially available kits such as Zen-Bio ORAC Anti-oxidant Assay kit (#AOX-2)). The Zen-Bio ORAC Anti-oxidant Assay kit measures the loss of fluorescein fluorescence over time due to the peroxyl-radical formation by the breakdown of AAPH (2,2'-axobis-2-methyl propanimidamide, dihydrochloride). Trolox, a water soluble vitamin E analog, serves as positive control inhibition fluorescein decay in a dose dependent manner.

Mushroom Tyrosinase Activity Assay:

In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (Sigma) can be incubated with its substrate L-Dopa (Fisher) in the presence or absence of each of the active ingredients, any one of the combination of ingredients, or compositions having said combinations disclosed in the specification. Pigment formation can be evaluated by colorimetric plate reading at 490 nm. The percent inhibition of mushroom tyrosinase activity can be calculated compared to non-treated controls to determine the ability of test ingredients or combinations thereof to inhibit the activity of purified enzyme. Test extract inhibition was compared with that of kojic acid (Sigma).

Matrix Metalloproteinase 3 and 9 Enzyme Activity (MMP3; MMP9) Assay:

An in vitro matrix metalloprotease (MMP) inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2-mercapto-4-methyl-pentanoyl]-LG-0C2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm ($\varepsilon=13,600$ M-1 cm-1 at pH 6.0 and above 7). The active ingredients, any one of the combination of ingredients, or compositions having said combinations disclosed in the specification can be assayed.

Matrix Metalloproteinase 1 Enzyme Activity (MMP1) Assay:

An in vitro matrix metalloprotease (MMP) inhibition assay. MMPs are extracellular proteases that play a role in many normal and disease states by virtue of their broad substrate specificity. MMP1 substrates include collagen IV. The Molecular Probes Enz/Chek Gelatinase/Collagenase Assay kit (#E12055) utilizes a fluorogenic gelatin substrate to detect MMP1 protease activity. Upon proteolytic cleavage, bright green fluorescence is revealed and may be monitored using a fluorescent microplate reader to measure enzymatic activity.

The Enz/Chek Gelatinase/Collagenase Assay kit (#E12055) from Invitrogen is designed as an in vitro assay to measure MMP1 enzymatic activity. The active ingredients, any one of the combination of ingredients, or compositions having said combinations disclosed in the specification can be assayed. The assay relies upon the ability of purified MMP1 enzyme to degrade a fluorogenic gelatin substrate. Once the substrate is specifically cleaved by MMP1 bright green fluorescence is revealed and may be monitored using a fluorescent microplate reader. Test materials are incubated in the presence or absence of the purified enzyme and substrate to determine their protease inhibitor capacity.

Cyclooxygenase (COX) Assay:

An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. The Colormetric COX (ovine) Inhibitor screening assay (#760111, Cayman Chemical) can be used to analyze the effects of each of the active ingredients, any one of the combination of ingredients, or compositions having said combinations disclosed in the specification on the activity of purified cyclooxygnase enzyme (COX-1 or COX-2). According to manufacturer instructions, purified enzyme, heme and test extracts can be mixed in assay buffer and incubated with shaking for 15 min at room temperature. Following incubation, arachidonic acid and colorimetric substrate can be added to initiate the reaction. Color progression can be evaluated by colorimetric plate reading at 590 nm. The percent inhibition of COX-1 or COX-2 activity can be calculated compared to non-treated controls to determine the ability of test extracts to inhibit the activity of purified enzyme.

Lipoxygenase (LO) Assay:

An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotrienes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid. The Colorimetric LO Inhibitor screening kit (#760700, Cayman Chemical) can be used to determine the ability of each of the active ingredients, any one of the combination of ingredients, or compositions having said combinations disclosed in the specification to inhibit enzyme activity. Purified 15-lipoxygenase and test ingredients can be mixed in assay buffer and incubated with shaking for 10 min at room temperature. Following incubation, arachidonic acid can be added to initiate the reaction and the mixtures can be incubated for an additional 10 min at room temperature. Colorimetric substrate can be added to terminate catalysis and color progression can be evaluated by fluorescence plate reading at 490 nm. The percent inhibition of lipoxyganse activity can be calculated compared to non-treated controls to determine the ability of each of the active ingredients, any one of the combination of ingredients, or compositions having said combinations disclosed in the specification to inhibit the activity of purified enzyme.

Elastase Assay:

EnzChek® Elastase Assay (Kit# E-12056) from Molecular Probes (Eugene, Oreg. USA) can be used as an in vitro enzyme inhibition assay for measuring inhibition of elastase activity for each of the active ingredients, any one of the combination of ingredients, or compositions having said combinations disclosed in the specification. The EnzChek kit contains soluble bovine neck ligament elastin that can be labeled with dye such that the conjugate's fluorescence can be quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide, N-methoxysuccinyl-Ala-Ala-Pro-Val-chloromethyl ketone, can be used as a selective, collective inhibitor of elastase when utilizing the EnzChek Elastase Assay Kit for screening for elastase inhibitors.

Oil Control Assay: An assay to measure reduction of sebum secretion from sebaceous glands and/or reduction of sebum production from sebaceous glands can be assayed by using standard techniques known to those having ordinary skill in the art. In one instance, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

Erythema Assay:

An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with the active ingredients, any one of the combination of ingredients, or compositions having said combinations disclosed in the specification. Repeat measurements can be taken at regular intervals to determine the formula's ability to reduce redness and irritation.

Skin Moisture/Hydration Assay:

Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance. Each of the active ingredients, any one of the combination of ingredients, or compositions having said combinations disclosed in the specification can be assayed according to this process.

Skin Clarity and Reduction in Freckles and Age Spots Assay:

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether each of the active ingredients, any one of the combination of ingredients, or compositions having said combinations disclosed in the specification is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay:

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay:

Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay:

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay with Methods Disclosed in Packman et al. (1978):

Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer:

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer:

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas:

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and are of the replicas covered by wrinkles or fine lines was determined.

Surface Contour of the Skin Assay with a Profilometer/Stylus Method:

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay:

In other non-limiting aspects, the efficacy of each of the active ingredients, any one of the combination of ingredients, or compositions having said combinations disclosed in the specification can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing each of the active ingredients, any one of the combination of ingredients, or compositions having said combinations disclosed in the specification or with the base alone as a control. Alternatively, an untreated sample of the skin analog can be used as a control.

Production of Filaggrin—

Changes in the production of filaggrin in keratinocytes due to each of the active ingredients, any one of the combination of ingredients, or compositions having said combinations disclosed in the specification can be measured. Filaggrin is the precursor to Natural Moisturizing Factor (NMF) in the skin. Increased NMF increases the moisture content of the skin. Filaggrin production in treated and non-treated keratinocytes can be determined using a bioassay that analyzes filaggrin concentration in keratinocyte cell lysates. A non-limiting example of a bioassay that can be used to quantify filaggrin production is the PROTEINSIMPLE® Simon™ western blotting protocol. For each sample, normal human epidermal keratinocytes (NHEK) are grown in EPI-200-Mattek Epilife® growth media with calcium from Life Technologies (M-EP-500-CA). NHEK are incubated in growth medium overnight at 37° C. in 5% $CO_2$ prior to treatment. NHEK are then incubated in growth medium with 1% test compound/extract or no compound/extract (negative control) for 24 to 36 hours. The NHEK can then be washed, collected, and stored on ice or colder until lysed on ice using a lysis buffer and sonication. The protein concentrations of the samples can be determined and used to normalize the samples. The lysates can be stored at −80° C. until use in the quantification assay.

The PROTEINSIMPLE® Simon™ western blotting bioassay assay employs a quantitative western blotting immunoassay technique using an antibody specific for filaggrin to quantitatively detect filaggrin in the test samples. Cell samples are lysed and normalized for protein concentration. Normalized samples and molecular weight standards can then be loaded and ran on a denatured protein separation gel using capillary electrophoresis. The proteins in the gel are immobilized and immunoprobed using a primary antibody specific for filaggrin. The immobilized proteins can then be immunoprobed with an enzyme-linked detection antibody that binds the primary antibody. A chemiluminescent substrate solution can then be added to the immobilized proteins to allow chemiluminescent development in proportion to the amount of filaggrin bound in the immobilization. The chemiluminescent development is stopped at a specific time and the intensity of the chemiluminescent signal can be measured and compared to positive and negative controls.

Production of Occludin—

Changes in the production of occludin in keratinocytes due to each of the active ingredients, any one of the combination of ingredients, or compositions having said combinations disclosed in the specification can be measured. Occludin is a protein critical to the formulation of tight junctions and the skin's moisture barrier function. A non-limiting example of how occludin production in treated and non-treated keratinocytes can be determined is by the use of a bioassay that analyzes occludin concentration in keratinocyte cell lysates. The bioassay can be performed using PROTEINSIMPLE® Simon™ western blotting protocol. For the samples, adult human epidermal keratinocytes (HEKa) from Life Technologies (C-005-5C) can be grown at 37° C. and 5% $CO_2$ for 24 hours in Epilife growth media with calcium from Life Technologies (M-EP-500-CA) supplemented with Keratinocyte Growth Supplement (HKGS) from Life Technologies (S-101-5). HEKa are then incubated in growth medium with test compound/extract, no compound/extract for negative control, or with 1 mM $CaCl_2$ for positive control for 24 to 48 hours. The HEKa are then washed, collected, and stored on ice or colder until lysed on ice using a lysis buffer and sonication. The protein concentrations of the samples can be determined and used to normalize the samples. The lysates are stored at −80° C. until use in the bioassay.

The PROTEINSIMPLE® Simon™ western blotting bioassay assay employs a quantitative western blotting immunoassay technique using an antibody specific for occludin to quantitatively detect occludin in the test samples. Cell samples are lysed and normalized for protein concentration. Normalized samples and molecular weight standards are then loaded and ran on a denatured protein separation gel using capillary electrophoresis. The proteins in the gel are then immobilized and immunoprobed using a primary antibody specific for occludin. The immobilized proteins are immunoprobed with an enzyme-linked detection antibody that binds the primary antibody. A chemiluminescent substrate solution is then added to the immobilized proteins to allow chemiluminescent development in proportion to the amount of occludin bound in the immobilization. The chemiluminescent development can be stopped at a specific time and the intensity of the chemiluminescent signal can be measured and compared to positive and negative controls.

Keratinocyte Monolayer Permeability—

Changes in the permeability of a keratinocyte monolayer due to each of the active ingredients, any one of the combination of ingredients, or compositions having said combinations disclosed in the specification can be measured. Keratinocyte monolayer permeability is a measure of skin barrier integrity. Keratinocyte monolayer permeability in treated and non-treated keratinocytes can be determined using, as a non-limiting example, the In Vitro Vascular Permeability assay by Millipore (ECM642). This assay analyzes endothelial cell adsorption, transport, and permeability. Briefly, adult human epidermal keratinocytes from Life Technologies (C-005-5C) can be seeded onto a porous collagen-coated membrane within a collection well. The keratinocytes are then incubated for 24 hours at 37° C. and 5% $CO_2$ in Epilife growth media with calcium from Life Technologies (M-EP-500-CA) supplemented with Keratinocyte Growth Supplement (HKGS) from Life Technologies (S-101-5). This incubation time allows the cells to form a monolayer and occlude the membrane pores. The media is then replaced with fresh media with (test sample) or without (non-treated control) test compounds/extracts and the keratinocytes are incubated for an additional 48 hours at 37° C. and 5% $CO_2$. To determine permeability of the keratinocyte monolayer after incubation with/without the test compound/extract, the media is replaced with fresh media containing a high molecular weight Fluorescein isothiocyanate (FITC)-Dextran and the keratinocytes are incubated for 4 hours at 37° C. and 5% $CO_2$. During the 4 hours incubation, FITC can pass through the keratinocytes monolayer and porous membrane into the collection well at a rate proportional to the monolayer's permeability. After the 4 hour incubation, cell viability and the content of FITC in the collection wells can be determined. For the FITC content, the media in the collection well is collected and fluorescence of the media determined at 480 nm (Em) when excited at 520 nm. Percent permeability and percent change in comparison to the non-treated controls can be determined by the following equations: Percent Permeability=((Mean Ex/Em of test sample)/Mean Ex/Em untreated control)*100; Percent Change=Percent Permeability of test sample−Percent Permeability of untreated control.

Production of Hyaluronic Acid—

Changes in the production of hyaluronic acid in human dermal fibroblasts due to each of the active ingredients, any one of the combination of ingredients, or compositions having said combinations disclosed in the specification can be measured. HA is a polysaccharide involved in stabilization of the structure of the matrix and is involved in providing turgor pressure to tissue and cells. As one non-limiting example, HA production in treated and non-treated adult human dermal fibroblasts (HDFa) cells can be determined using the Hyaluronan DuoSet ELISA kit from R&D Systems (DY3614). In this assay, for production of samples, subconfluent HDFa cells from Cascade Biologics (C-13-5C) are incubated at 37° C. and 10% $CO_2$ in starvation medium (0.15% fetal bovine serum and 1% Penicillin Streptomycin solution in Dulbecco's Modified Eagle Medium) for 72 hours prior to treatment. The cells are then incubated with fresh starvation medium with either test compound, positive control (phorbol 12-myristate 13-acetate from Sigma-Aldrich (P1585) and platelet derived growth factor from Sigma-Aldrich (P3201)), or no additive for 24 hours. Media is then collected and frozen at −80° C. until use in the ELISA assay.

Briefly, the ELISA assay employs a quantitative sandwich enzyme immunoassay technique whereby a capture antibody specific for HA can be pre-coated onto a microplate. Standards and media from treated and untreated cells are pipetted into the microplate wells to enable any HA present to be bound by the immobilized antibody. After washing away any unbound substances, an enzyme-linked detection antibody specific for HA is added to the wells. Following a wash to remove any unbound antibody-enzyme reagent, a substrate solution is added to the wells to allow color development in proportion to the amount of HA bound in the initial step. The color development is stopped at a specific time and the intensity of the color at 450 nm can be measured using a microplate reader.

Inhibition of Hyaluronidase Activity—

Changes in the activity of hyaluronidase due to each of the active ingredients, any one of the combination of ingredients, or compositions having said combinations disclosed in the specification can be measured. Hyaluronidase is an enzyme that degrades HA. HA is a polysaccharide involved in stabilization of the structure of the matrix and is involved in providing turgor pressure to tissue and cells. As one non-limiting example, hyaluronidase activity can be determined using an in vitro protocol modified from Sigma-Aldrich protocol # EC 3.2.1.35. Briefly, hyaluronidase type 1-S from Sigma-Aldrich (H3506) is added to microplate reaction wells containing test compound or controls. Tannic acid can be used as a positive control inhibitor, no test compound can be added for the control enzyme, and wells with test compound or positive control but without hyaluronidase can be used as a background negative control. The wells are incubated at 37° C. for 10 minutes before addition of substrate (HA). Substrate is added and the reactions incubated at 37° C. for 45 minutes. A portion of each reaction solution is then transferred to and gently mixed in a solution of sodium acetate and acetic acid pH 3.75 to stop that portion of the reaction (stopped wells). The stopped wells and the reaction wells should both contain the same volume of solution after addition of the portion of the reaction solution to the stopped wells. Both the reaction wells and the stopped wells are incubated for 10 minutes at room temperature. Absorbance at 600 nm is then measured for both the reaction wells and the stopped wells. Inhibition can be calculated using the following formulas: Inhibitor (or control) activity=(Inhibitor stopped wells absorbance at 600 nm−inhibitor reaction wells absorbance at 600 nm); Initial activity=control enzyme absorbance at 600 nm; Percent Inhibition=[(Initial activity/Inhibitor Activity)*100]−100.

Peroxisome Proliferator-Activated Receptor Gamma (PPAR-γ) Activity—

Changes in the activity of PPAR-γ due to each of the active ingredients, any one of the combination of ingredients, or compositions having said combinations disclosed in the specification can be measured. PPAR-γ is a receptor critical for the production of sebum. As one non-limiting example, the activity of PPAR-γ can be determined using a bioassay that analyzes the ability of a test compound or composition to inhibit binding of a ligand. Briefly, fluorescent small-molecule pan-PPAR ligand, FLUORMONE™ Pan-PPAR Green, available from Life Technologies (PV4894), can be used to determine if test compounds or compositions are able to inhibit binding of the ligand to PPAR-γ. The samples wells include PPAR-γ and fluorescent ligand and either: test compound or composition (test); a reference inhibitor, rosiglitazone (positive control); or no test compound (negative control). The wells are incubated for a set period of time to allow the ligand opportunity to bind the PPAR-γ. The fluorescence polarization of each sample well can then be measured and compared to the negative control well to determine the percentage of inhibition by the test compound or composition.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Cosmetic Ingredient Dictionary, Third Edition, CTFA, 1982
International Cosmetic Ingredient Dictionary, Fourth edition, CTFA, 1991
International Cosmetic Ingredient Dictionary and Handbook, Tenth Edition, CTFA, 2004
International Cosmetic Ingredient Dictionary and Handbook, Twelfth Edition, CTFA, 2008

The invention claimed is:

1. A method of reducing oxidative damage of skin comprising applying to oxidant damaged skin a topical composition comprising encapsulated resveratrol, oligopeptide-1, and niacinamide, wherein the combination of encapsulated resveratrol, oligopeptide-1, and niacinamide reduces oxidative damage in the skin, and wherein the oligopeptide-1 comprises the sequence of caprooyl-Gly-His-Lys-Lys.

2. The method of claim 1, wherein the oligopeptide-1 inhibits tyrosinase, increases production of elastin, stimulates collagen production and/or secretion, and/or inhibits TNF-α; and niacinamide inhibits melanogenesis.

3. The method of claim 1, wherein the topical composition is applied to the skin daily.

4. The method of claim 1, wherein the topical composition comprises 0.00001 to 0.1% by weight of encapsulated resveratrol, 0.0000001 to 0.01% by weight of oligopeptide-1, and 0.001 to 3% by weight of niacinamide.

5. The method of claim 4, wherein the topical composition is formulated as a sunscreen and further comprises 5 to 15% by weight of homosalate, 1 to 10% by weight each of ethylhexyl salicylate and oxybenzone, 0.1 to 10% by weight each of butyl methoxydibenzoylmethane and octocrylene, 0.1 to 5% by weight each of dicapryl carbonate, dimethicone, ammonium acryloyldimethyltaurate/VP copolymer, cetearyl alcohol, and ceteareth-25, 0.01 to 3% by weight each of disodium ethylene dicocamide PEG-15 disulfate, silica, and caprylyl glycol, and 0.01 to 1% by weight each of bisabolol, and tocopheryl acetate.

6. The method of claim 4, wherein the topical composition is formulated as a day moisturizer and further comprises 10 to 15% by weight of isopropyl palmitate and 0.1 to 10% by weight each of glyceryl stearate, PEG-100 stearate, butylene glycol, glycerine, methyl trimethicone, silica, mica, ammonium acryloyldimethyltaurate/VP copolymer, lauryl PEG-9 polydimethylsiloxyethyl dimethicone, isostearyl neopentanoate, cetyl phosphate, and triethanolamine.

7. The method of claim 4, wherein the composition is formulated as a night moisturizer and further comprises 0.01 to 15% by weight of dimethicone, 0.01 to 10% by weight of isohexadecane, 0.1 to 10% by weight of aluminum starch octenylsuccinate, and 0.01 to 5% by weight each of caprylic/capric triglyceride, cetearyl alcohol, glyceryl stearate, butylene glycol, and hydroxyacetophenone.

8. The method of claim 4, wherein the topical composition is formulated as a cleanser and comprises 0.1 to 10% by weight each of acrylates copolymer, cocoamidopropyl betaine, propanediol, and PPG-2-hydroxyethyl coco/isostearamide, and 0.01 to 1% by weight each of *Copernicia cerifera* (Carnauba) wax, sodium chloride, and lactose.

9. The method of claim 4, wherein the topical composition is formulated as a foundation and further comprises 20 to 40% by weight of cyclopentasiloxane and 1 to 15% by weight each of titanium dioxide, butylene glycol, PEG-9 dimethicone, trimethylsiloxysilicate, lauryl methacrylate/glycol dimethacrylate crosspolymer, PEG/PPG-20/15 dimethicone, magnesium sulfate, and polymethylsilsesquioxane.

10. The method of claim 1, wherein the composition is an emulsion.

11. The method of claim 1, wherein the emulsion is an oil-in-water emulsion.

12. The method of claim 1, wherein the composition is a cream or lotion.

13. The method of claim 1, wherein the composition is a gel.

14. The method of claim 1, wherein the composition is a solution.

15. The method of claim 1, wherein the composition comprises 25 to 98% by weight of water.

16. The method of claim 1, wherein the composition is applied to a fine line or wrinkle.

* * * * *